United States Patent [19]
Fox

[11] Patent Number: 5,882,351
[45] Date of Patent: Mar. 16, 1999

[54] FASTENERS HAVING COORDINATED SELF-SEEKING CONFORMING MEMBERS AND USES THEREOF

[75] Inventor: William Casey Fox, Pipe Creek, Tex.

[73] Assignee: BioMedical Enterprises, Inc., San Antonio, Tex.

[21] Appl. No.: 797,591

[22] Filed: Feb. 7, 1997

Related U.S. Application Data

[63] Continuation of PCT/US96/15722, Sep. 27, 1996 published as WO97/11651 Apr. 3, 1997 which is a continuation-in-part of Ser. No. 536,461, Sep. 29, 1995.

[60] Provisional application No. 60/042,914, Sep. 29, 1995.

[51] Int. Cl.⁶ ................................................ A61B 17/68
[52] U.S. Cl. ................................ 606/63; 606/60; 606/72
[58] Field of Search .................................. 606/62, 63, 64, 606/65, 66, 67, 68, 61, 72, 73, 60

[56] References Cited

U.S. PATENT DOCUMENTS

| | | |
|---|---|---|
| 2,077,804 | 4/1937 | Morrison . |
| 2,381,050 | 8/1945 | Hardinge . |
| 2,490,364 | 12/1949 | Livingston . |
| 2,631,584 | 3/1953 | Purificato . |
| 2,685,877 | 8/1954 | Dobelle . |
| 2,699,774 | 1/1955 | Livingston . |
| 3,024,785 | 3/1962 | Dobelle . |
| 3,216,414 | 11/1965 | Street . |
| 3,497,953 | 3/1970 | Weissman . |
| 3,505,921 | 4/1970 | Wigam . |
| 3,708,883 | 1/1973 | Flander . |
| 3,760,802 | 9/1973 | Fischer et al. . |
| 3,779,239 | 12/1973 | Fischer et al. . |
| 3,791,380 | 2/1974 | Dawidowski . |
| 3,805,775 | 4/1974 | Fischer et al. . |
| 3,986,504 | 10/1976 | Avila . |
| 4,091,806 | 5/1978 | Aginsky . |
| 4,204,531 | 5/1980 | Aginsky . |
| 4,220,712 | 9/1980 | Staffolani . |

(List continued on next page.)

FOREIGN PATENT DOCUMENTS

| | | |
|---|---|---|
| 0 317 688 A1 | 5/1989 | European Pat. Off. . |
| 2387638 | 12/1978 | France . |
| 2606269 A1 | 5/1988 | France . |
| 1075793 | 2/1960 | Germany . |
| 2117604 | 10/1972 | Germany . |
| 28 21 785 | 11/1979 | Germany . |
| 587915 | 1/1959 | Italy . |
| 1055498 A | 11/1983 | Russian Federation . |
| 1127582 A | 12/1984 | Russian Federation . |
| 1255116 A1 | 9/1986 | Russian Federation . |
| 1386182 A1 | 4/1988 | Russian Federation . |
| 1524880 A1 | 11/1989 | Russian Federation . |
| 1436546 | 5/1976 | United Kingdom . |
| WO 97/11651 | 4/1997 | WIPO . |

OTHER PUBLICATIONS

Olerud et al., "Internal Fixation of Femoral Neck Fractures—Two Methods Compared," *The Journal of Bone and Joint Surgery* (Br.) 73B:16–19 (1991).

Sargon Enterprises, Inc., Excerpts from Catalog entitled Sargon Immediate Load Implant (date unknown).

*Primary Examiner*—Guy V. Tucker
*Attorney, Agent, or Firm*—Akin, Gump, Strauss, Hauer & Feld, L.L.P

[57] ABSTRACT

Fasteners having coordinated self-seeking conforming members or implanting into a cavity such as a hole, tube, or hard tissue defect are provided. An actuator mechanism translates applied force to conform members of a plurality of members to the cavity. The fasteners may be used for implanting a prosthetic device into hard tissue of humans or animals, for anchoring a device while the device is being worked on, for centering a device in a hole or tube, such as in well technology. The mechanism operates expanding members so that they independently or dependently conform and apply controlled and known pressure to surrounding materials.

25 Claims, 22 Drawing Sheets

U.S. PATENT DOCUMENTS

| | | |
|---|---|---|
| 4,227,518 | 10/1980 | Aginsky . |
| 4,236,512 | 12/1980 | Aginsky ................................... 606/68 |
| 4,237,875 | 12/1980 | Termanini . |
| 4,261,350 | 4/1981 | Branemark et al. . |
| 4,275,717 | 6/1981 | Bolesky . |
| 4,309,136 | 1/1982 | Talan . |
| 4,330,891 | 5/1982 | Branemark et al. . |
| 4,409,974 | 10/1983 | Freedland . |
| 4,498,468 | 2/1985 | Hansson . |
| 4,519,100 | 5/1985 | Wills et al. . |
| 4,523,587 | 6/1985 | Frey . |
| 4,590,930 | 5/1986 | Kurth et al. . |
| 4,632,101 | 12/1986 | Freedland . |
| 4,681,590 | 7/1987 | Tansey . |
| 4,721,103 | 1/1988 | Freedland . |
| 4,862,883 | 9/1989 | Freeland . |
| 5,013,242 | 5/1991 | Prezmecky . |
| 5,057,103 | 10/1991 | Davis . |
| 5,059,193 | 10/1991 | Kuslich . |
| 5,064,425 | 11/1991 | Branemark et al. . |

Interfacial Pressure:

$$\frac{Torque \times 0.085 \times \cos(\beta) \times \cos((25 - \alpha\_reference) + \beta) \times (0.075 - (0.085 \times \cos(25 - \alpha\_index) - (0.085 \times \cos(\alpha\_reference_0))))}{0.109 \times 0.11 \times (0.15 - (0.085 \times \cos(25 - \alpha\_index)) - (0.085 \times \cos(25 - \alpha\_reference))) - (0.085 \times \cos(25 - \alpha\_reference_0)) - (0.085 \times \cos(\alpha\_reference) - (0.085 \times \cos(\alpha\_reference_0))) \times 0.25}$$

Fig. 11

FASTENERS HAVING COORDINATED SELF-SEEKING CONFORMING MEMBERS AND USES THEREOF

This application is a continuation application based on PCT/US96/15722 filed Sep. 27, 1996, published as WO97/11651 Apr. 3, 1997, which is a continuation-in-part application of U.S. Ser. No. 08/536,461, filed Sep. 29, 1995, which claims priority to provisional application U.S. Ser. No. 60/042,914 filed Sep. 29, 1995. The patent applications are incorporated by reference herein.

FIELD OF THE INVENTION

The present invention relates to fasteners having coordinated self-seeking conforming members and uses thereof. The fasteners may be used for anchoring a prosthesis, or for centering or aligning a structure within a hole, tube, or cavity. In particular, hard tissue implant fasteners are envisioned for attaching a prosthesis to bone or cartilage. Methods of using said fasteners are also provided.

BACKGROUND OF THE INVENTION

Prior art references relate to structures adapted to expand the radial projection of the device after the device has been inserted into a cavity. Three groups of prior art are outlined by structural similarities in their expansion characteristics. A fourth group relates to other expansion characteristics.

Axial contraction is used to produce radial expansion once a device has been inserted into a cavity. Wigam (U.S. Pat. No. 3,505,921) and Talan (U.S. Pat. No. 4,309,136) disclose construction fastening devices. Fischer et al. (U.S. Pat. No. 3,779,239) and Rublenik (SU 1,386,182-A) relate to elongated fasteners that employ radial expansion elements at the distal end of the device. These fasteners are intended to secure fractured portions of bone tissue. Kuslich (U.S. Pat. No. 5,059,193) relates to a spinal implant for use between vertebrae. Tansey (U.S. Pat. No. 4,681,590) relates to a structure having metal strips secured between an upper plate and a nut. The nut is mounted on a screw and constrained against rotation so that rotating the screw reduces the axial separation of the nut and upper plate causing the metal strips to expand radially. Tansey also relates to a femoral stem prosthesis.

Oblique contact has been used between moving elements to expand the radial projection of devices that have been inserted into a cavity. One common example of this type of fastener is from Aginsky (U.S. Pat. No. 4,091,806). In this mechanism, a central shaft is displaced relative to an outer concentric shaft. The central shaft includes a wedge that obliquely contacts a longitudinally slotted portion of the outer concentric shaft. The oblique contact translates the axial force on the wedge into a radial force that expands the outer concentric shaft radially. Prior art having multiple elements actuate the elements such that the elements cannot be expanded independently to adapt to the contours of the cavity in which they are placed.

Pivotal connections have been used to expand the radial projection of devices once they are inserted into a cavity. Prior art relates to elements pivotally connected to the device that are contacted by an axially displaceable element. The axial force at a distance from the pivotal connection creates a torque that rotates the pivotally connected elements into a new position that has a greater radial diameter. Some of these references disclose mechanisms that also use oblique contact to provide the necessary torque. As examples of this type of mechanism, see Avila (U.S. Pat. No. 3,986,504), Davis (U.S. Pat. No. 5,057,103), Dobelle (U.S. Pat. Nos. 2,685,877 and 3,024,785), and Firer (SU 1,524,880A). None of the references in this group relate to means for coordinated self-seeking conforming of elements. Aginsky (U.S. Pat. Nos. 4,204,531 and 4,227,518) relate to use of pivotal connections in a different structure. A pivot point is movably mounted in a longitudinal slot. The pivot point is pivotally coupled to two legs that are pivotally coupled at their other ends to two sections of the outer sheath. When the outer sheath is displaced axially, the pivot point is constrained by the slot and the sections of the outer sheath are rotated radially by the legs. This structure does not allow coordinated self-seeking conforming actuation of the two outer sheath sections.

Bolesky (U.S. Pat. No. 4,275,717) and Street (U.S. Pat. No. 3,215,414) relate to elements that are biased to expand radially. These elements are elastically constrained by a ring or cap that is axially displaced once the device is inserted so that the biased elements can resume a radially expansive position. Erlich-DeGuemp (FR 2,387,638) relates to a device that uses the bone tissue surface to provide an oblique contact for radial expansion. Muhlbayer (DT 1,075,793) relates to use of a rotating central shaft to translate a band which has three pinned elements that are allowed to rotate radially. The pinned elements can rotate freely but are not driven by a mechanism and do not provide a means to engage the three rotating elements in a coordinated self-seeking conforming manner.

A review of the product literature shows adaptations of mechanism similar to Livingston (U.S. Pat. Nos. 2,699,774 and 2,490,364), Fisher (U.S. Pat. No. 3,805,775) and Flander (U.S. Pat. No. 3,708,883). An Alta Modular Trauma System product (Howmedica, Rutherford, N.J.) uses a slotted sleeve, wedge shaped inner mandrel and translation of the mandrel in the sleeve to increase radial diameter. Other companies are generally introducing unicortical fasteners (engages only one bony cortex) consisting of a slotted externally threaded hollow cylinder with a threaded inner mandrel that when rotated expands the radial diameter of the outer cylinder. One example of this type of device is the Sargon Implant system (Sargon Enterprises, Inc., Beverly Hills, Calif.).

Bone implants have been used to solve health care problems of orthopedic and maxillofacial reconstruction, prosthesis fixation, drug delivery and fracture stabilization. Heretofore, bone and cartilage (hard tissue) implants were fastened with screw threads, interference fits, uniformly expanding mechanisms and cement. The majority of these devices and associated techniques provide poor initial fixation, and following bone formation around the device, provide good fixation but often for only a limited period of time. Implant removals are frequently performed following failure of the bone-implant interface and clinical loosening of the device.

The principal cause for implant failure in hard tissue is the separation of bone from the surface of the implant. Bone resorption about an implant is induced by micromotion of the device relative to the surrounding hard tissue, adverse tissue reaction to the implant material, or tissue necrosis due to drill heating and mechanical stress concentrations. Micromotion is often due to poor initial stabilization of a threaded, interference fit or cemented device.

Bone and cartilage are tissues with viscoelastic material properties. Their modulus of elasticity and ultimate strength are much less than the metal and ceramic materials used for hard tissue implants. This mismatch in material properties is a factor in device-tissue interfacial micromotion, interface stress concentration and implant loosening. This problem is compounded by bone's range of morphology and material properties.

The bone organ contains two distinct types of bone tissue. Cortical bone is the hard structural bone that forms the outer shell of the skeleton. Cancellous bone is contained within cortical bone and makes up a significant portion of the volume of most bones. Cancellous bone is porous, trabecular in structure, highly vascular, filled with cellular elements and undergoes active remodeling (formation and resorption).

Heretofore bone implants placed transverse to the long axis of bone penetrated a short segment of the cortical bone shell and had a significant portion of their surface adjacent to cancellous bone. These devices relied on both the cortical and cancellous bone for initial and long-term stability. Implant dependence on porous low strength cancellous bone and limited cortical bone contact causes poor device stability.

Heretofore bone implants that were placed along the long central axis of bone were designed to occupy much of the cancellous bone space and contact the endosteal surface (inner surface) of cortical bone. The irregular morphology of the endosteal surface caused point-contacts and concentrated loads between these devices and cortical bone. Initial implant fixation was achieved by interference fit at these points of contact.

High concentrated loads and stress-shielding between point-contacts can cause resorption of bone and implant loosening. Long-term implant fixation is dependent on cancellous bone growth around the surface of the implant where it is not contacting the endosteal surface of cortical bone.

Cements are commonly used to fill the void between the endosteal surface of cortical bone and the implant. Though commonly used, cements can cause adverse tissue reactions and complicate the load characteristics of the bone-implant interface by adding a third material with its unique material properties. Uncemented devices are being introduced for hip and knee prostheses. Some of these devices are contoured or require the endosteal surface of the cortical bone to be machined to increase the implant-to-cortical bone surface area. Contouring the device surface increases its cost and may require patient imaging and bone shaping. Machining bone removes healthy tissue and weakens the structural strength of the organ. Additionally, local heating of bone during machining can cause its death.

Hand-tool reaming, press-fit installation and cementing require skill. These procedures are sources of surgical variance and potential prostheses failure. The combined issues of device design, device-bone interface failure, micromotion, stress-concentration, stress-shielding material property differences and surgical variance limit the useful lifetime of many prostheses to 5 to 20 years.

The present invention addresses these problems in the prior art and provides devices having coordinated self-seeking conforming members, where a known relationship exists between the pressure exerted on the surrounding material and the mechanism engagement torque or force, and having the ability to contour to an irregular defect.

SUMMARY OF THE INVENTION

The present invention provides fasteners having coordinated self-seeking conforming members for conforming to a cavity. An actuator mechanism coordinates and translates applied force for the independent or dependent movement of each member. The process of conforming also aligns the fastener, and thereby aligns that which is attached to the fastener. The present fasteners are useful wherever implants are desired, and wherever aligning is needed. In particular, the fasteners are useful for hard tissue implants for humans and animals, such as cartilage and bone implants for anchoring prostheses; and for aligning devices as in industrial technology.

An embodiment of the present invention provides a fastener for implanting into a cavity, the fastener comprising a body; a plurality of members movably connected to the body, each member being independently movable for coordinated self seeking conforming to the cavity; and an actuator mechanism for coordinating and translating applied force to each member.

As used herein, a "fastener" may also be referred to as an implant; a "cavity" is an enclosed space for receiving and holding a structure and may be a hoe, tube, cylinder, well, hard tissue defect, or the like. A "hard tissue defect" is a defect in bone or cartilage that may have been constructed surgically, by accident, or from disease. "Independently movable for coordinated self-seeking conforming to a cavity" means that each member responds to applied force in a coordinated manner until it engages a wall of the cavity and a second member may continue to move until it also engages a wall of the cavity. "Coordinated" means that all members move initially in response to applied force. "Self-seeking" means that a member moves in response to an applied force until it engages a wall of the cavity for independent movement. "Conforming" means that a member engages a wall of the cavity. "Movably connected" means directly or indirectly connected. A member may be a lever, a finger, a projection, a protrusion, a wing, a shoe, or an ear, or the like.

In a preferred embodiment, an interfacial pressure exists between each member and the cavity when in use. In an even more preferred embodiment where the cavity is a hard tissue defect, a sufficient interfacial pressure exists between each member and the cavity to cause hard tissue density, in particular, bone density, to increase when in use.

The actuator mechanism may further comprise a locking mechanism for locking the actuator mechanism. The locking mechanism may be selected from the group consisting of a cap, a jam nut, a taper, a transverse pin, a key, a spline, an abutment, and the like.

Where the cavity is a hard tissue defect, the fastener as describe herein may further comprise a prosthesis connected to the fastener. The prosthesis may be a hard tissue trauma fixation device or hardware selected from the group consisting of a dental implant, a spinal prosthesis, an intermedullary rod, a knee prosthesis, a shoulder prosthesis, a finger prosthesis, a hip prosthesis, a temporal-mandibular joint, a dental implant with prosthetic tooth, a plate, a port, and the like.

A further embodiment of the present invention includes a fastener as described herein having a first member and a second member and wherein the actuator mechanism comprises a journal; and a first link and a second link, each link rotatingly and slidingly joined to the journal, the first link rotatingly joined to the first member and the second link rotatingly joined to the second member such that when the journal is moved, the first link and the second link move and cause the first member and the second member to move independently to conform to the cavity. The actuator mechanism may further comprise a bearing having a bore for housing the journal, the journal further having an end movably connected to the bearing so that when the bearing is moved, the journal moves through the bore of the bearing.

The invention includes a fastener as described herein having a first member and a second member and wherein the actuator mechanism comprises a journal; and a cam slidingly and rotatingly connected to the journal, the cam further slidingly and rotatingly joined to the first member and to the second member such that when the journal is moved, the cam moves and causes the first member and the second member to move independently to conform to the cavity. The actuator mechanism may further comprise a bearing having a bore for housing the journal, the journal further having an end movably connected to the bearing so that when the bearing is moved, the journal moves through the bore of the bearing.

Another embodiment is a fastener as herein described having a first member and a second member and wherein the actuator mechanism comprises a journal; a first link having a first end and a second end, the first end pivotally connected to the journal; a second link having a first end and a second end, the first end pivotally connected to the second end of the first link, and the second end pivotally connected to the first member; and a third link having a first end and a second end, the first end pivotally connected to the second end of the first link, and the second end pivotally connected to the second member, wherein when the journal is moved, the first link moves and acts on the second link and the third link to cause the first member and the second member to move independently to conform to the cavity. The actuator mechanism may further comprise a bearing having a bore for housing the journal, the journal further having an end movably connected to the bearing so that when the bearing is moved, the journal moves through the bore of the bearing.

A further fastener of the present invention as herein described has a first member and a second member and wherein the actuator mechanism comprises a journal; a first link having a first end and a second end, the first end pivotally and slidingly connected to the journal, and the second end pivotally connected to the first member; and a second link having a first end and a second end, the first end pivotally and slidingly connected to the journal, and the second end pivotally connected to the second member; wherein when the journal is moved, the first link and the second link move to cause the first member and the second member to move independently to conform to the cavity. The actuator mechanism may further comprise a bearing having a bore for housing the journal, the journal further having an end movably connected to the bearing so that when the bearing is moved, the journal moves through the bore of the bearing.

The fastener as herein described having a first member and a second member is an aspect of the invention wherein the actuator mechanism comprises a journal; and a cam having a first slot and a second slot, the first slot slidingly and pivotally connected to the journal, and the second slot slidingly and pivotally joined to the first member and to the second member such that when the journal is moved, the cam moves and causes the first member and the second member to move independently to conform to the cavity. The actuator mechanism may further comprise a bearing having a bore for housing the journal, the journal further having an end movably connected to the bearing so that when the bearing is moved, the journal moves through the bore of the bearing.

The fastener as herein described having a first member and a second member, each member having an arm, is an aspect of the invention, wherein the actuator mechanism comprises a shaft having a first end and a second end, and a component constrained to be in slidable contact with the second end of the shaft and in contact with the arm of each member such that when the shaft is moved, the component moves in contact with the arms and causes the first member and the second member to move independently to conform to the cavity. In a preferred embodiment, the shaft decreases in diameter at the second end.

A further aspect of the invention is a fastener as described herein having a first member and a second member, each member having an angled surface, and wherein the single actuator mechanism comprises a shaft having a first end and a second end; and a component constrained by the angled surface of each member to be in slidable contact with the second end of the shaft such that when the shaft is moved, the component moves in contact with the members and causes the first member and the second member to move independently to conform to the cavity. In this embodiment, each member is movably limited by the body such that the component is contained within the body by the angled surface of each member. In a preferred embodiment, the shaft decreases in diameter at the second end.

A further embodiment of the invention is a fastener for implanting into a cavity, the fastener comprising a body comprising a movable structure; a plurality of members rotatingly connected to the movable structure, each member being independently movable with respect to the body for coordinated self-seeking conforming to the cavity; and an actuator mechanism within the movable structure for coordinating and translating applied force to conform independently each member to the cavity, the actuator mechanism comprising a journal rotatingly and slidingly connected to each member such that when the journal is moved through the bore of the body, each member moves symmetrically with respect to the movable structure and moves independently with respect to the body to conform to the cavity.

An embodiment of the invention is a fastener for implanting into a cavity, the fastener comprising a body; a plurality of members movably connected to the body, each member being dependently movable for coordinated self-seeking conforming to the cavity; and an actuator mechanism for coordinating and translating applied force to each member. "Dependently movable" means that the members move at the same time, when one member engages a wall of the cavity, a second member is not able to move further. For dependent movement, "self-seeking" means that movement of members is determined by a first member engaging a wall of the cavity. Further members do not continue to move.

A further embodiment is a fastener having dependent movement as herein described having a first member and a second member and wherein the actuator mechanism comprises a journal rotatingly and slidingly joined to the first member and to the second member such that when the journal is moved, the first member and the second member move dependently to conform to the cavity.

A further fastener having dependent movement has a first member and a second member and wherein the actuator mechanism comprises a journal; a first link having a first end and a second end, the first end pivotally connected to the journal, and the second end pivotally connected to the first member; and a second link having a first end and a second end, the first end pivotally connected to the journal, and the second end pivotally connected to the second member; wherein when the journal is moved, the first link and the second link move to cause the first member and the second member to move dependently to conform to the cavity.

A further fastener having dependent movement has a first member and a second member, each member having an arm, wherein the actuator mechanism comprises a shaft having a first end and a second end, the second end being in slidable contact with the arm of each member such that when the shaft is moved, the first member and the second member move dependently to conform to the cavity.

A further fastener having dependent movement has a first member and a second member, each member having an angled surface, and wherein the actuator mechanism comprises a shaft having a first end and a second end, the second end being in slidable contact with the angled surface of each member such that when the shaft is moved, the first member and the second member move dependently to conform to the cavity.

In each of the fastener embodiments having dependent movement, the actuator mechanism may further comprise a bearing having a bore for housing the journal, the journal further having an end movably connected to the bearing so that when the bearing is moved, the journal moves through the bore of the bearing.

A further embodiment of the invention is a fastener for securing a structure to a cavity where the structure is configured to fit to an outer surface of the cavity. The fastener comprises a body having a first bore and a slot opening onto the first bore; a cylinder within the first bore, the cylinder having a driving mechanism; a member within the slot, the member movably connected to the body and acted on by the driving mechanism for conforming to the cavity; and wherein when a force is applied to the cylinder, the driving mechanism causes the member to move to conform to the cavity, thereby securing the structure to the cavity. The driving mechanism may comprise an actuator, the member may comprise a lobe, and in this case, the actuator meshes with the lobe of the member. In a preferred embodiment, the driving mechanism comprises a worm gear, the member comprises a plurality of gear teeth, and the worm gear meshes with the gear teeth of the member. The fastener may further comprise a locking means for locking the cylinder within the bore. The locking means may be selected from the group consisting of a retainer or a jam nut. The structure may be a prosthesis and may be selected from the group of prostheses described herein.

Materials suitable for fabrication of a fastener of the present invention may be a material that is at least biocompatible for the length of intended use, and has sufficient structural strength. A biocompatible material is selected from the group consisting of a metal, a ceramic, a polymer, and a combination thereof. Where the fastener is formed of a metal, the metal is titanium, titanium alloy, stainless steel, chromium cobalt, chromium cobalt alloy, or the like. Where the fastener is formed of a ceramic, ceramic is silica glass, alumina, calcium phosphate, calcium carbonate, or the like. Where the fastener is formed of a polymer, the polymer is delrin, nylon, polyester, polymethylmethacrylate, polyethylene, or the like.

Use of the fasteners of the present invention for implanting in a cavity and aligning the fastener within the cavity is an aspect of the invention. The use comprises placing the fastener into the cavity and applying force to conform each member of the plurality of members to the cavity thereby aligning the fastener with the cavity. The cavity may be related to industry, or a hard tissue defect such as a bone or cartilage defect.

Use of the fasteners of the present invention, where the cavity is a hard tissue defect of an animal, for fastening a prosthesis to the hard tissue defect is an aspect of the invention. The use comprises placing the fastener into the hard tissue defect of the animal; applying force to conform each member of the plurality of members to the cavity; and attaching the prosthesis to the fastener. Preferably, the animal is a human. In a preferred embodiment, a sufficient interfacial pressure exists between each member and the cavity to cause hard tissue density to increase when in use.

Use of the fasteners of the present invention for fastening airplane skin at a cavity site is an aspect of the present invention. The use comprises placing the fastener into a cavity of airplane skin; and applying force to conform each member of the plurality of members to the cavity thereby fastening the airplane skin.

Use of the fasteners of the present invention for aligning a part to an object in automated production is a further aspect of the present invention. The use comprises placing the fastener onto the part; and applying force to the fastener to conform each member of the plurality of members to align the part to the object. In a preferred embodiment, the object is a robot or part thereof.

Several significant advantages are achieved by the present invention. The fasteners of the present invention, when implanted in bone tissue, for example, provide unique and novel designs that minimize micromotion, optimize the stress distribution to bone, allow material property matching through active mechanisms, assist in centering the device, present forces to the bone to stimulate it to become more dense, minimize or eliminate surgical variance and allow it to be tightened, if loose. Applied force to the fastener may be from a tool attached to the fastener. The tool may push on the actuator mechanism to cause the members to move.

The efficiency of the fastening device of the present invention is improved considerably by the provision of its design and its operational compatibility with bone. Further advantages include independent movement of the expansion members for certain embodiments, conformation of the implant-to-bone defect, application of a known bone-to-implant interfacial pressure, capability to reengage or disengage the mechanism to refasten or remove the implant, drawing of the implant into the defect by the action of the expansion components, compression of small irregularities along walls of the hole or defect by the expanding components to increase contact area, high implant surface area against the surrounding material, control of implant alignment or centering within the defect, and firm initial fixation. All of these advantages are accomplished without bending any implant component. This minimizes the likelihood of component failure through residual stress in the device and fatigue loading. These advantages are significant when compared to press-fit, screw thread and uniformly expanding fasteners.

Following long-standing patent law convention, the terms "a" and "an" mean "one or more" when used in this application, including the claims.

BRIEF DESCRIPTION OF THE DRAWINGS

Further objects and advantages of this invention will become apparent from consideration of the drawings and ensuing description of the preferred embodiments.

FIG. 9a shows the fastener ready for insertion in an extraction site. FIG. 9b shows the implant with its members partially engaged and operating out-of-phase from one another.

FIG. 11 provides an equation for calculating interfacial pressure.

DETAILED DESCRIPTION OF THE PREFERRED EMBODIMENTS

Figure 1A:
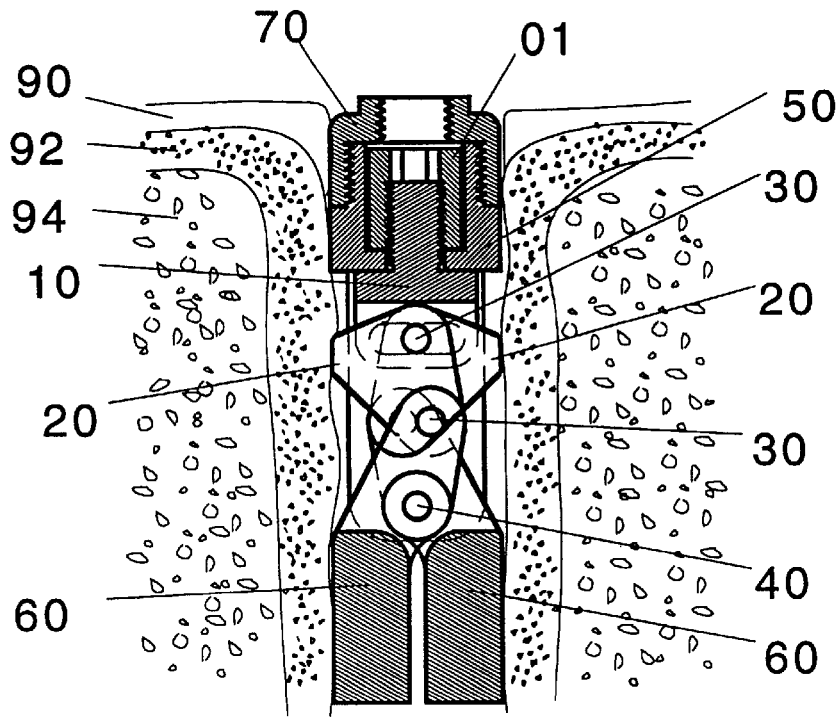
FIG. 1a and FIG. 1b are cross-sectional plane views of a fastener having a linkage-member mechanism in bone and configured as a bone contacting dental implant.

In a preferred embodiment, the present invention provides a fastening method and device for bone so designed as to impart a considerably improved efficiency under substantially all attachment conditions. An understanding of the orthopaedic problem; bone biology, physiology, and anatomy; and mechanical engineering and materials science have led to the development of novel devices that are nonobvious because of the diverse technical experience required to combine this knowledge into a solution to this long studied and difficult medical problem.

Studies of bone biology and physiology have demonstrated the sensitivity of bone cells to mechanical loads. Excessive loads cause tissue death and resorption, modest loads cause increases in density and strength as described by Wolf's Law, while physiologically low skeletal loads cause bone resorption, porosity and weakening (as in microgravity-induced osteoporosis). Orthopaedic practice commonly requires fasteners for use in regular (drill hole) or irregular shaped (fracture) bone defects. Prior art technology is suboptimal with breakage and loosening a common problem.

In the present invention, material properties of static and fatigue strength, biocompatibility and toxicity have been combined with the mechanical requirements of the fastener to complement the physiology and biology of bone and meet the general needs of orthopaedic medicine for prostheses and implants that are located on, within or through bone or cartilage.

The fastener allows controlled expansion of its members, the adaptation of components of the device to the surrounding tissue, and the ability to determine the bone-to-implant interfacial pressure. Implant expansion is driven by the surgeon. The expanding components, most commonly consisting of pinned rotating members, may operate independently or dependently. Once expanding components are contacting bone, the installation force or torque can be used to compute the bone-to-implant interfacial pressure.

The mechanical load exerted by the members on the margins of the bone defect is such that the force applied by the members is within a range that will not fracture bone or cause it to deteriorate, and is sufficiently great so as to fly fasten the structure and stimulate bone to become more dense.

Several embodiments of the actuator mechanism are provide herein and are intended not to limit the device design but to broaden its scope by including examples of mechanisms with means to facilitate the present invention. In particular, a bearing is an optional aspect of the fasteners of the present invention. Different actuator mechanisms allow for either independent or dependent movement of members, as described herein.

Fastener Having a Linkage-Member Actuator Mechanism: An embodiment of the fastener of the present invention (FIG. 1a, FIG. 1b) includes an assembly having a single internal actuator mechanism including a bearing (01) with internally threaded bore, an externally threaded journal (10) having a transverse slot adjacent to one end, and two links (20) that when joined with pins (30) to the slot in the journal (10) and members (60) and constrained to rotate about a second pin (40) within a lower body (50) together are capable of causing members (60) to move independently of one another so as to engage, conform, press upon, and be retractable from, surrounding material, The bearing (01) is constrained within the upper body (70) and lower body (50) so as to contain the mechanism and resist fixation forces applied to the members (60).

Figure 1B:
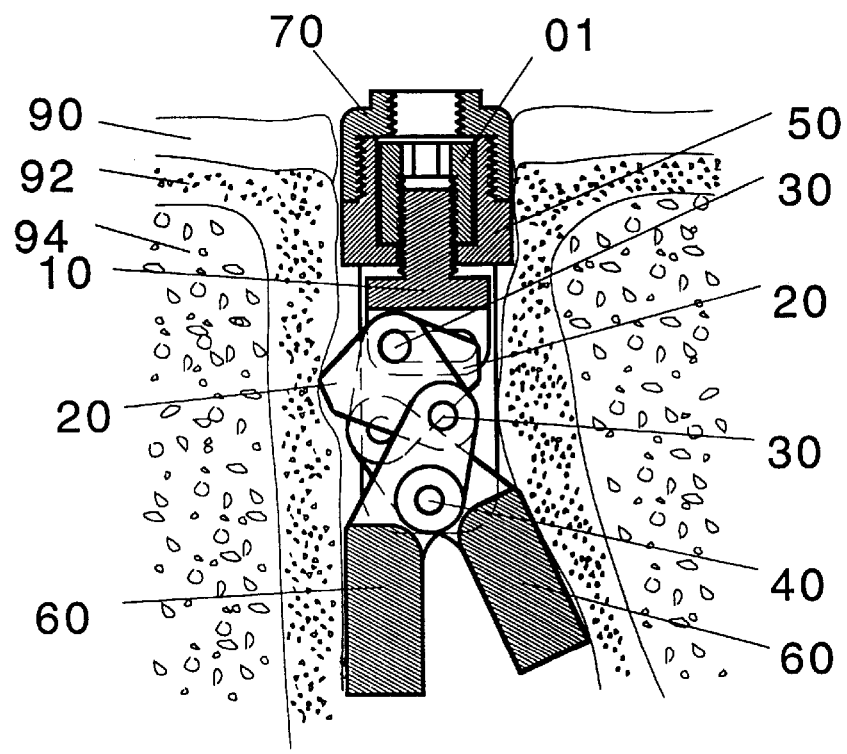

The embodiment of FIG. 1a and FIG. 1b is shown in a drilled hole in a mandible with gingival tissue (90), compact bone (92) and cancellous bone (94) surrounding the implanted fastener. In a drilled hole the members (60) expand equally to contact the surrounding compact bone. In a tooth extraction site where the defect is irregular in its shape, the members (60) operate independently and conform to the defect as shown in FIG. 1b.

In the operation of the present embodiment, when the bearing (01) is "tightened" by rotating about its central axis within the bore of the lower housing (50), the journal (10) is forced to move out of the bore of the bearing (01). Translation of the journal (10) causes the linkages (20) to cause the members to rotate about pin (40) and engage the surrounding bone (92). If one of the members (60) contacts surrounding bone (92) then the linkages (20) begin to slide and rotate about pin (30) thus allowing the member (60) which was not in contact with bone (92) to continue its rotation about in (40) until it conforms to and contacts bone (92). Once both members (60) contact bone (92) then additional rotation of the bearing (01) loads the journal (10) causing a predictable force to be applied by the members (60) to the surrounding bone (92).

Fastener Having a Cammed-Member Actuator Mechanism: A Further embodiment of the actuator mechanism (FIG. 2) is shown configured as a femoral prosthesis placed in the medullary compartment of the femur (194). The mechanism includes a bearing (100) having an internally threaded bore, externally threaded journal (110) having a journal pin (115) near one end, and a cam with slot (120) that together are capable of causing each of two members (130) to move independently of one another so as to engage, conform and press upon and, if disengaged, retract from surrounding cancellous bone (190) or cortical bone (192).

This embodiment uses an upper housing (140) and lower housing (150) to contain the bearing (100) and support the movement of the members (130). The members (130) are pivotally connected to the lower half of the housing (150) with pins (160) and to the cam (120) with a second set of pins (170). The cam (120) is further connected to the journal (110) by a journal pin (115).

This embodiment is combined with a femoral ball (106) and carrier (102) to complete the prosthesis. To ensure security of the mechanism a jam nut (180) is provided to lock the mechanism so as to prevent rotation of the bearing (100).

In the operation of the present embodiment, when the bearing (100) is "tightened," the journal (110) is forced to move out of the bore of the bearing (100). The cam (120) is linearly moved by its pin (115) connection with the journal (110) causing the members (130) to be rotated about the pivotal connections (160) with the housing (150). When a first member (130) contacts a contour of the bone tissue cavity in its rotation, the cam (120) tilts and slides to allow continued rotation of the second member (130) as well as continued linear movement of the journal (110). Once both members (130) contact the contours of the bone tissue cavity, additional downward force on the journal (110) is balanced by the resistive force caused by contact of the bone (192). A means of locking the mechanism can be achieved by a cap (180) that is fixed to the housing to contact and resist the rotation of the bearing (100).

Figure 3:
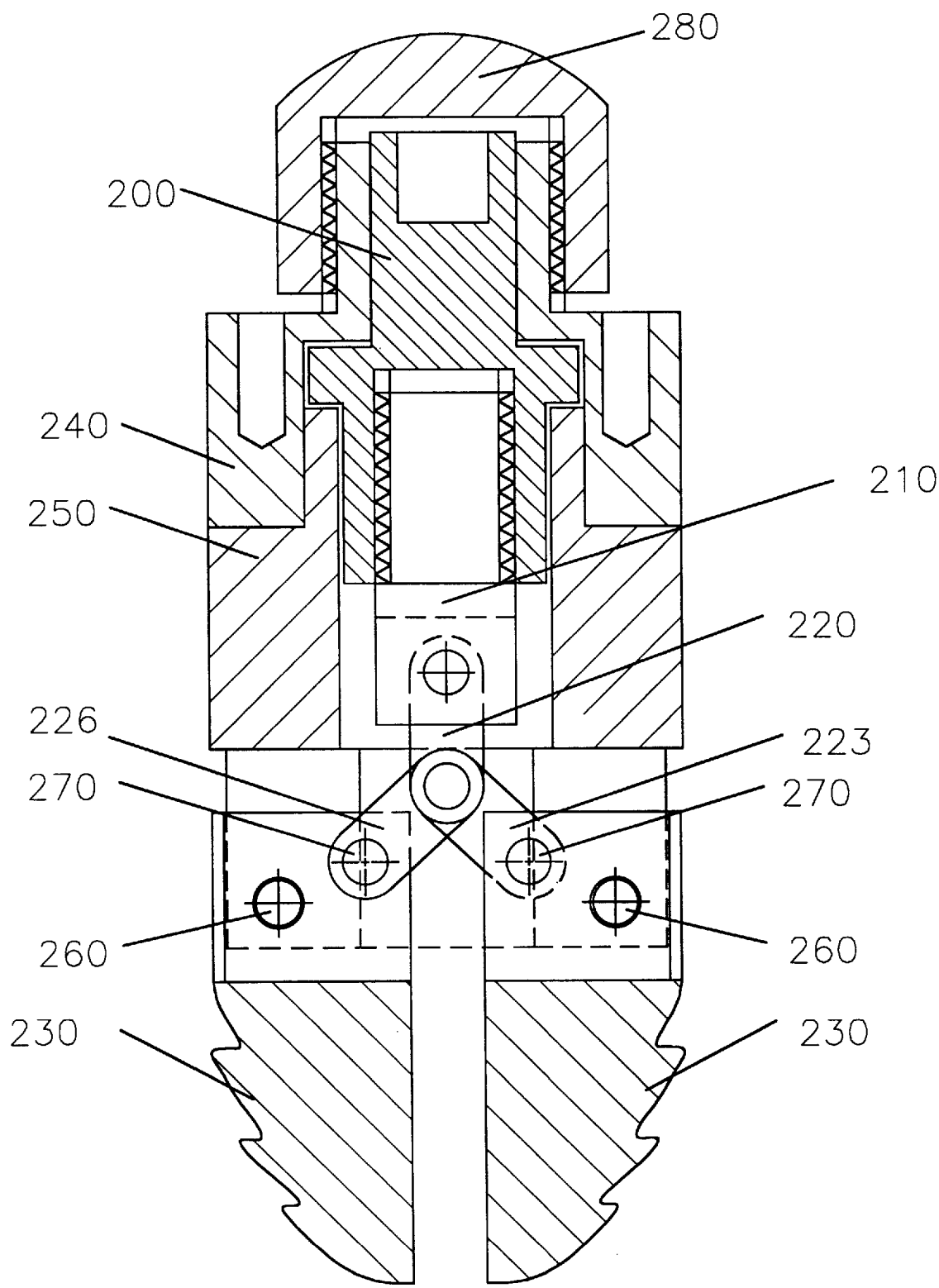
FIG. 3 is a cross-sectional plane view of a fastener having a three-linkage mechanism configured as the mandibular component of a temporal-mandibular joint.
Figure 4:
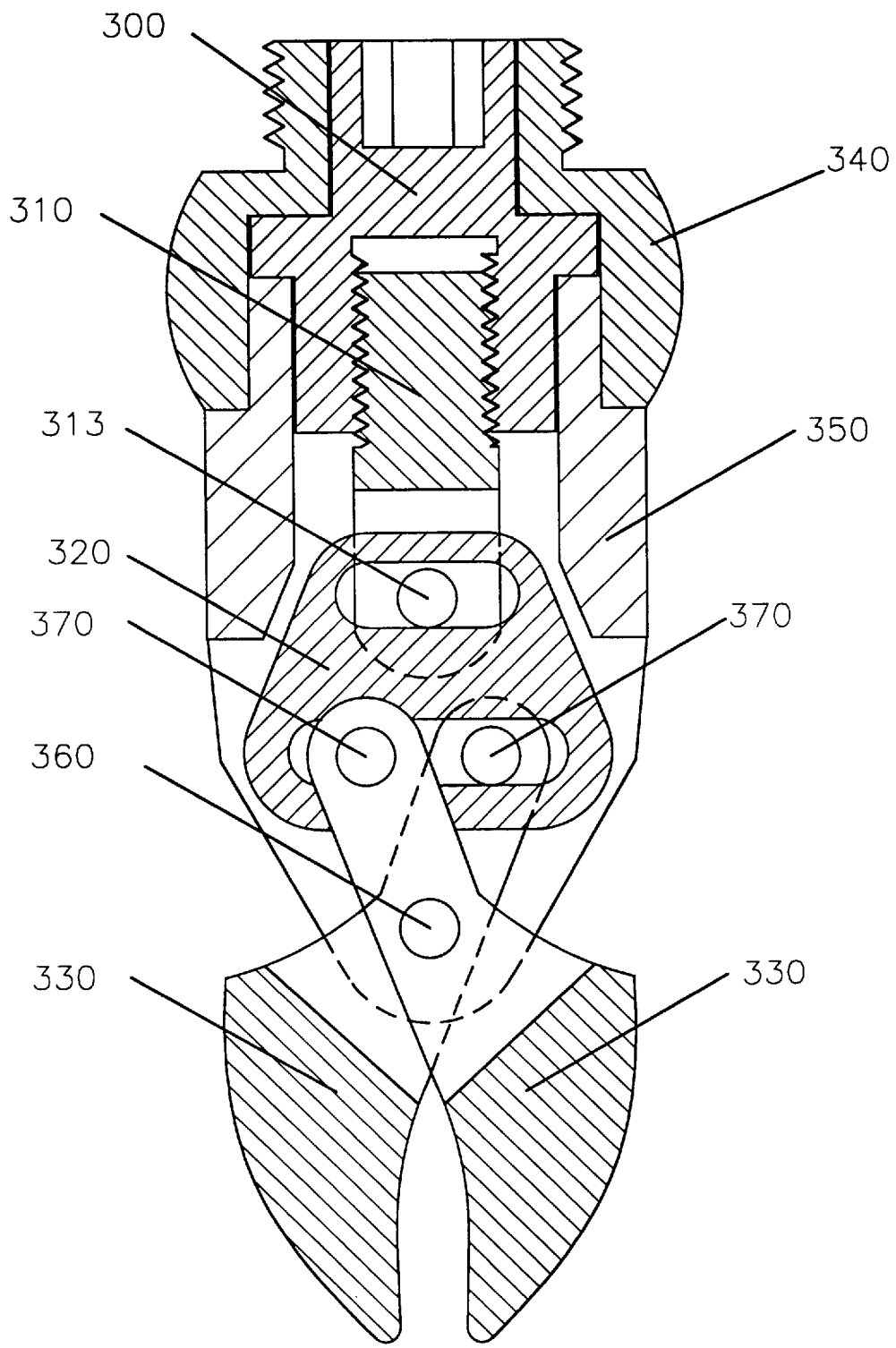
FIG. 4 is a cross-sectional plane view of a fastener with scissoring members and a two slot cam mechanism.

Fastener Having a Three-Linkage Actuator Mechanism: A further embodiment of a fastener of the present invention uses an internal mechanism consisting of a bearing (200), externally threaded journal (210), and three linkages (220, 223 and 226) to operate the members (FIG. 3).

This embodiment uses a housing to contain the mechanism and support the movement of the conforming portion of the device. In this embodiment the housing includes an upper (240) and lower half (250) with members (230) pivotally connected to the lower half of the housing (250) with pins (260).

The upper (240) and lower (250) housing have a bore. In this bore a bearing (200) with an internally threaded bore engages an externally threaded journal (210) which is pivotally coupled to one of the linkages (220) with a pin (263). This linkage is pivotally coupled with a pin (266) to each of two linkages (223 and 226) which are pivotally coupled at their second end to each of the members (230) with pins (270). Translation of the journal (210) causes independent expansion of the members (230).

In the operation of the present embodiment, when the bearing (200) is "tightened," the journal (210) is forced to move out of the bore of the bearing (200) causing the linkage (220) that is pivotally connected to the journal to move. The translational and rotational movement of this linkage (220)

causes the other two linkages (223 and 226) to move. Movement of the three linkages (220, 223 and 226) together cause the members (230) to move independently into the surrounding tissue.

Figure 23:
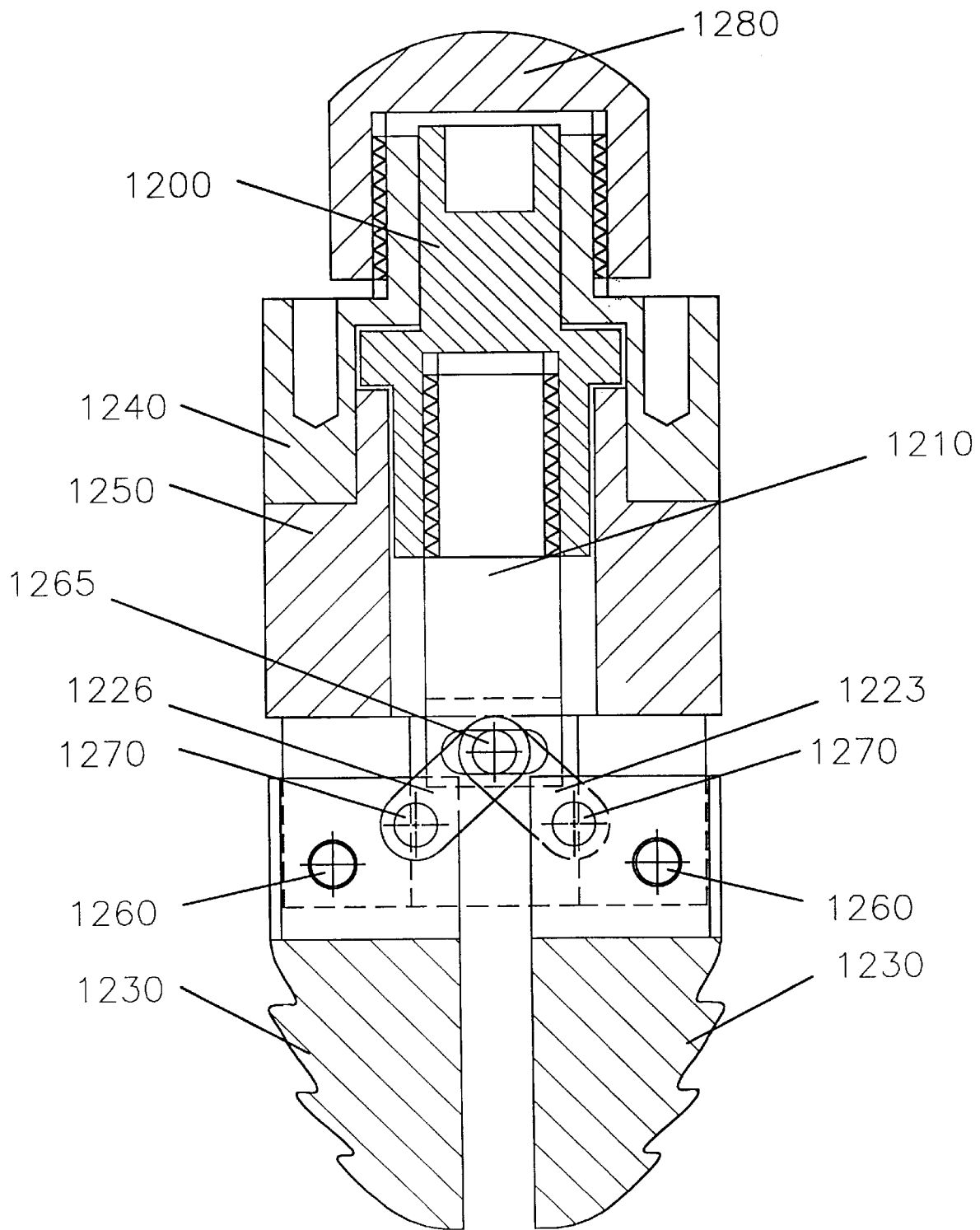
FIG. 23 shows a cross-sectional plane view of a fastener including an actuator mechanism using two links running in an actuator slot to allow coordinated self-seeking independent expansion of its members.

Fastener having Journal-Double Linkage Actuator Mechanism: In FIG. 23 is shown an upper body (1240), lower body (1250), journal or actuator (1210), cap (1001), member (1230), links (1223 and 1226), and pins (1260), (1265) and (1270). The actuator pin (1265) is slidingly and rotatingly connected to links (1223 and 1226). This embodiment is similar to that of FIG. 3, however, it is more simply made and is configured for independent self-seeking movement of the members (1060). When in use, the bearing (1200) is turned, forcing actuator (1210) out of its bore which causes actuator pin (1265) to rotatingly slide in the actuator slot causing links (1226) and (1223) to act on members (1230) so as to cause them to rotate about pin (1260).

Fastener Having a Two-Slot Cam Actuator Mechanism: A further fastener uses a housing to contain the mechanism and support the movement of the conforming portion of the device. As with the other embodiments, the housing consists of an upper (340) and lower half (350) with members (330) pivotally connected to the lower half of the housing (350) with a single pin (360) that is centrally located.

The upper housing (340) and lower housing (350) have a bore. In this bore a bearing (300) with an internally threaded bore engages an externally threaded journal (310) which is coupled to a cam (320) having a plurality of slots with a pin (313) that is further coupled to each of the members (330) with pins (370). The (320) shows a different configuration than previous embodiments having a pivotal siding connection to the journal pin (313) and a second pivotal sliding connection to the two members (330) with pins (370). This cam (320) configuration is applicable to other embodiments and in contrast to the preferred first and second embodiments the common pivot pin (360) of the member provides greater initial leverage in its unexpanded configuration.

In the operation of the present embodiment, when the bearing (300) is "tightened," the journal (310) is forced to move out of the bore of the bearing (300). The cam (320) is linearly moved by its connection with the journal (310) and the members (330) are rotated outward about the pivotal connection (360) with the housing (350). When one member (330) contacts a contour of the bone tissue cavity in its rotation, the cam (320) tilts to allow continued rotation of the other member (330) as well as continued linear movement of the journal (310). Once both members (330) contact the contour of the bone tissue cavity, additional downward force applied by the journal (310) is balanced by the resistive force of the bone tissue contacts.

Fastener Having a Sphere-Shaft Actuator Mechanism with Scissoring Members: A further embodiment uses a sphere (420) to actuate members (430). This embodiment uses a one-piece housing (440) to contain the mechanism and support the movement of the conforming portion of the device. This housing has members (430) pivotally connected with a single pin (460) that is centrally located in the housing (440).

The housing (440) has a bore with internal threads over a portion of its length and an internal taper that expands to the level of the pin (460) which is the pivot connection between the members (430) and the housing (440). In this bore externally threaded shaft (400) engages the internal threads. This shaft (400) contacts a sphere (420) that is constrained by the housing (440) and the upper arms (410) of the members (430). This sphere (420) rides between the upper arms (410) of the members (430). The shaft (400), sphere (420) and members (430) act together to independently expand the two members (430) from the centerline of the housing (440). The shaft (400) can be replaced with an unthreaded member and used in a housing (440) with an unthreaded bore allowing an implant holding instrument to push on this member and translate the ball (420). An abutment (470) locks the shaft (400) and provides a support for cement (490) and prosthetic tooth (480).

In the operation of the present embodiment, when the shaft (400) is turned, the sphere (420) is forced to move out of the bore of the housing (440). The force on the sphere (420) is transferred through the arms (410) of the members (430) to produce rotation of the members (430) about the central pin (460). When one member (430) contacts a contour of the bone tissue cavity in its rotation, the sphere (420) slides on the stationary arm (410) as it continues rotation of the noncontacting member (430). Once both members (430) contact the contours of the bone tissue cavity, additional downward force applied by the shaft (400) is balanced by the resistive force of the bone tissue contacts.

Fastener Having a Sphere-Shaft Actuator Mechanism with Pinned Members: A further embodiment uses a sphere (510) to cause two members (530) to swing away from the housing (540). This embodiment uses a one piece housing (540) to contain the mechanism and support the movement of the conforming portion of the device. This housing has members (530) each pivotally connected with pins (560).

The housing (540) has a bore with internal threads. In this bore an externally threaded shaft (500) engages the internal threads. This shaft (500) contacts a sphere (510) that is constrained by the opposing faces of the members (530). This sphere (510) rides between members (530). The shaft (500), sphere (510) and members (530) act together to independently expand the two members (530) from the centerline of the housing (540). An abutment (570) locks the shaft (500) and provides a support for cement (590) and prosthetic tooth (580). The implant is shown in a tooth extraction site surrounded with gingival tissue (592), compact bone (594) and cancellous bone (596).

In the operation of the present embodiment, when the shaft (500) is turned, the sphere (510) is forced to move out of the bore of the housing (540). The force on the sphere (510) is transferred through the sphere (510) to the members (530) to produce rotation of the members (530) about the pins (560). When one member (530) contacts a contour of the bone tissue cavity in its rotation, the sphere (510) slides on the stationary member (530) as it continues rotation of the noncontacting member (530). Once both members (530) contact the contours of the bone tissue cavity, additional downward force applied by the shaft (500) is balanced by the resistive force of the bone tissue contacts. The rotation of the members (530) is limited by contact between the housing (540) and members (530). This range is limited so that the sphere (510) cannot be pushed past the members (530) and out of the mechanism.

Fastener with Mechanism in a Spherical Rotating Housing Configured in a Structure: A further fastener can be used to secure a structure, for example a bone plate (650), to the surface of a bone (692). This embodiment uses a spherical body (620) having two members (630). The spherical body (620) is pivotally connected within the plate (650) with a cap (640) having a bore with a spherical internal surface which supports the movement of the members (630). Together the movement of the members (630) and the pivoting of the sphere (620) between the plate (650) and cap (640) allows the members (630) to independently conform to a body cavity.

The spherical body (620) has a bore. Within this bore is a bearing (600) with an internally threaded bore. This bearing (600) is held within the bore of the sphere (620) with a locknut (680) having a bore. In the bore of the bearing (600) an externally threaded journal (610) engages the internal threads. This journal (610) is pivotally and slidingly connected to members (630) with pins (670). The member (630) are pivotally connected to the spherical body (620) with pins (660) and act together to symmetrically expand from the centerline in relationship to the spherical body (620). The rotation of the spherical body (620) combined with the symmetrical expansion of the members (630) with respect to the spherical body (620) allows independent expansion of the members (630) with respect to the plate (650) and conformation to the bone (692).

In the operation of the present embodiment, when the bearing (600) is turned, the journal (610) is forced to move out of the bore of the spherical body (620). The movement of the journal (610) causes the members (630) to rotate about pins (660). When one member (630) contacts a contour of the bone tissue cavity in its rotation, the spherical body (620) rotates in the plate (650) to allow the noncontacting member (630) to continue to move. Once both members (630) contact the contours of the bone tissue cavity, additional downward force applied by the journal (610) is balanced by the resistive force of the bone tissue contacts.

Fastener with Worm Gear and Pinion Mechanism Configured in a Structure: A further embodiment can be used to secure a body (700), for example a plate, port or other structure, to the surface of a bone (780). This embodiment uses a geared mechanism consisting of a drive cylinder (710) having a worm gear, member (730) having gear teeth (720), locking nut (750), member pin (760) and retainer (770). Two or more geared mechanisms can be used with a body (700).

The members (730) are pivotally connected to the body (700) with pins (760). The geared teeth (720) of the members (730) protrude into separate bores cut through the body (700) at its periphery. A drive cylinder (710) is located in each bore allowing a worm gear cut on the drive cylinder (710) to mesh with the gear teeth (720) of the members (730). The drive cylinder is retained and locked into the bore with retainer (770) and locknut (750). The ability to actuate each member independently allows the members (730) of the implant to conform to a body cavity and hold the port (700) in place. In the design of this embodiment the separate drive cylinders (710) can be replaced by a common drive cylinder so as to rotate each member (730) simultaneously.

In the operation of the present embodiment, prior to placing the locknut (750), when the drive cylinder (710) is turned, the worm gear drives the gear teeth (720) and causes the member (730) to rotate. When one member (730) contacts a contour of the bone tissue cavity in its rotation the noncontacting members (730) can be actuated to rotate using the drive cylinder. Once both members (730) contact the contours of the bone tissue cavity, additional rotational torque applied by the drive cylinder (710) is balanced by the resistive force of the bone tissue contacts. Once engaged the locknut (750) is placed to stop any further rotation of the drive cylinder (710) or member (730).

Figure 22:
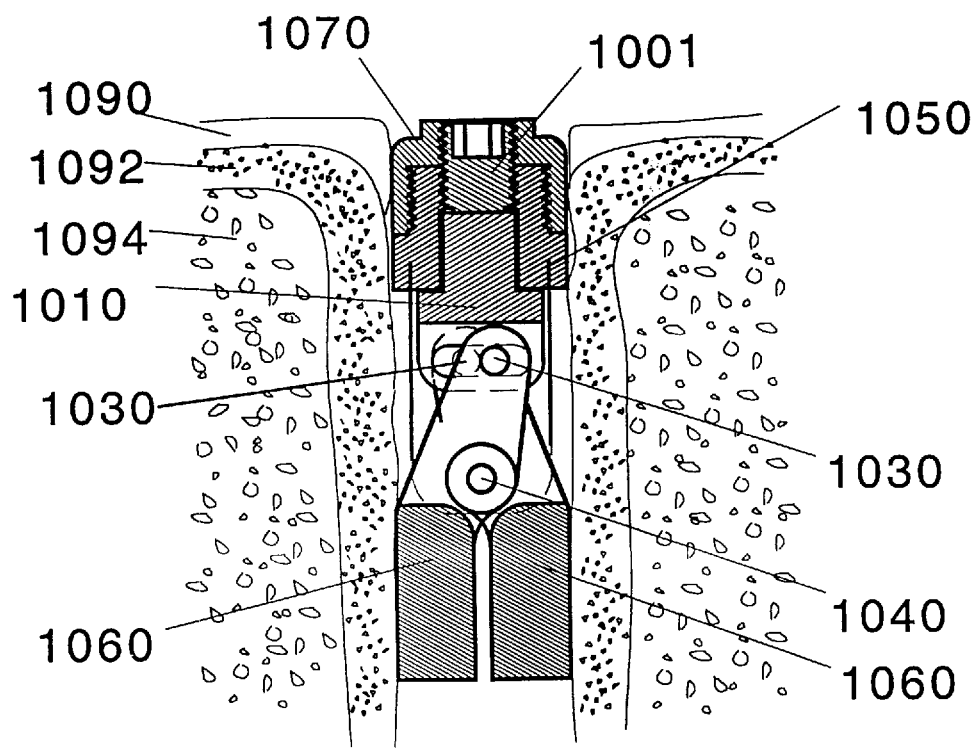
FIG. 22 shows a cross-sectional plane view of a fastener similar of FIG. 1 configured for dependent movement of its members. The first link and second link 20 of FIG. 1 have been removed to convert the actuator mechanism to dependent movement.

Fastener having Journal-Member Actuator Mechanism for Dependent Movement of Members: In FIG. 22 is shown an upper body (1070), lower body (1050), journal or actuator (1010), jam nut (1001), member (1060), and pins (1030) and (1040). This embodiment is similar to that of FIG. 1, however, it is configured for dependent movement of the members (1060). When the actuator (1010) is pushed through the lower body (1050), pins (1030) slidingly rotate in the actuator (1010) slot causing members (1060) to precess about pin (1040) in a dependent and symmetric manner.

Figure 24:
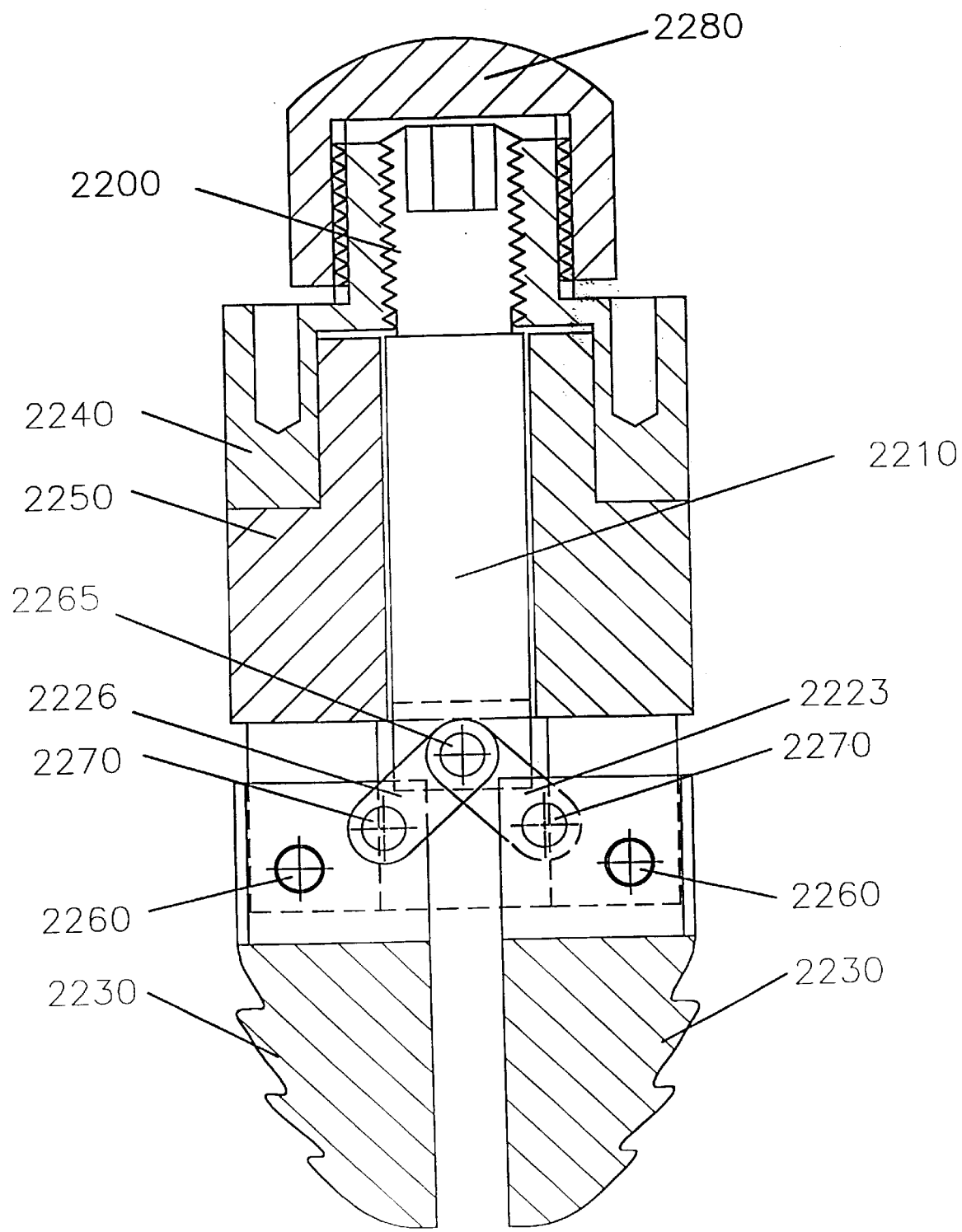
FIG. 24 shows a cross-sectional plane view of the fastener of FIG. 23 where the slot has been changed to be a press-fit pin thus allowing the coordinated self-seeking dependent expansion of its members.

Fastener having Journal-Double Linkage Actuator Mechanism for Dependent Movement of Members: In FIG. 24, the fastener of FIG. 23 has been modified to change the journal or actuator slot to a pin hole to receive pin (2265). This causes a rotational connection between links (2223) and (2226) that causes dependent symmetrical movement of members (2230) about pin (2260). When in use, actuator (2210) is pushed through the lower body (2250) causing the actuator pin (2265) to act on links (2226) and (2223) so as to cause members (2230) to rotate about pin (2260).

Figure 5:
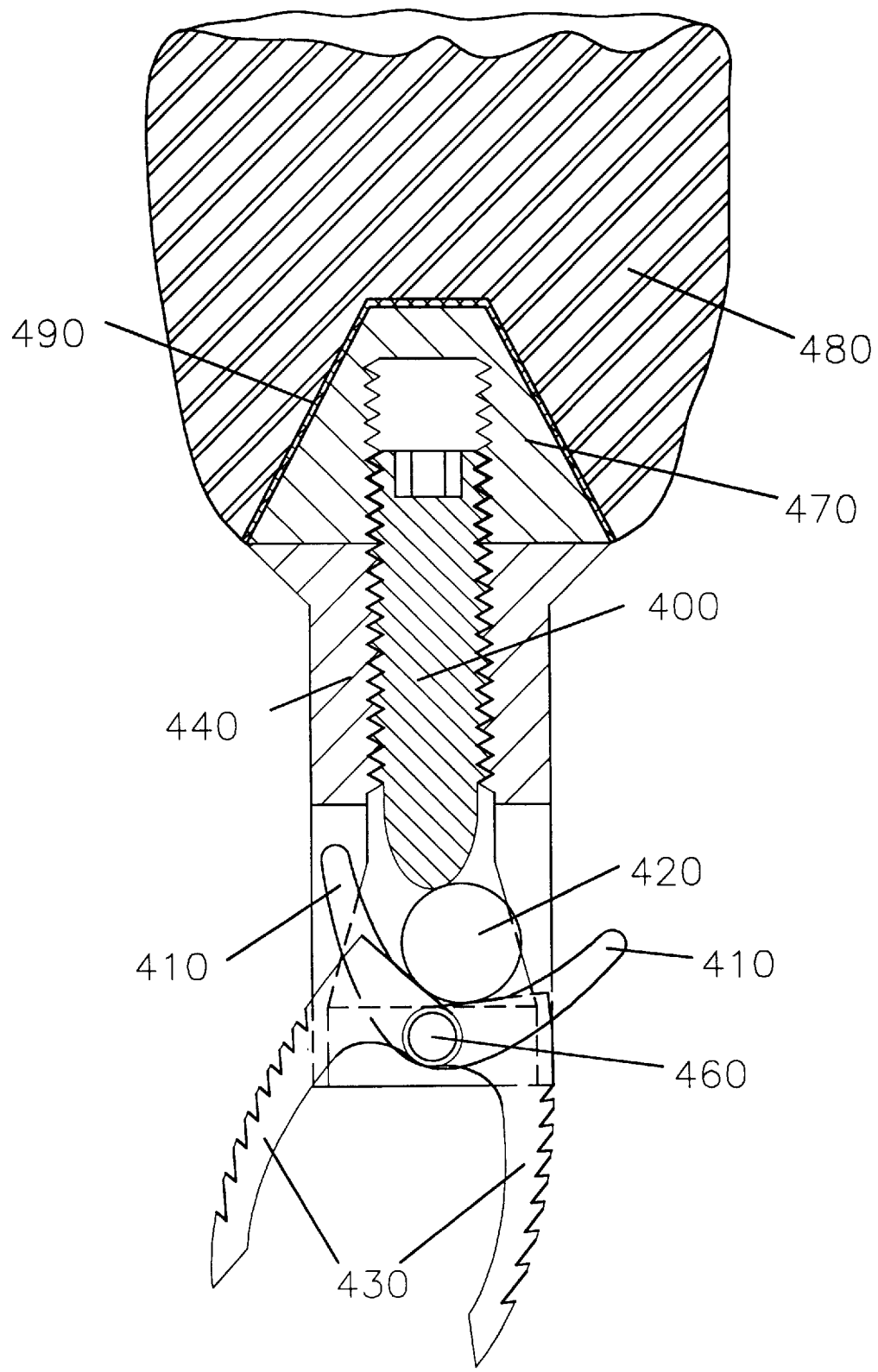
FIG. 5 is a cross-sectional plane view of a fastener with scissoring members, and sphere and shaft actuator mechanism configured as a bone-contacting dental implant with prosthetic tooth.
Figure 6A:
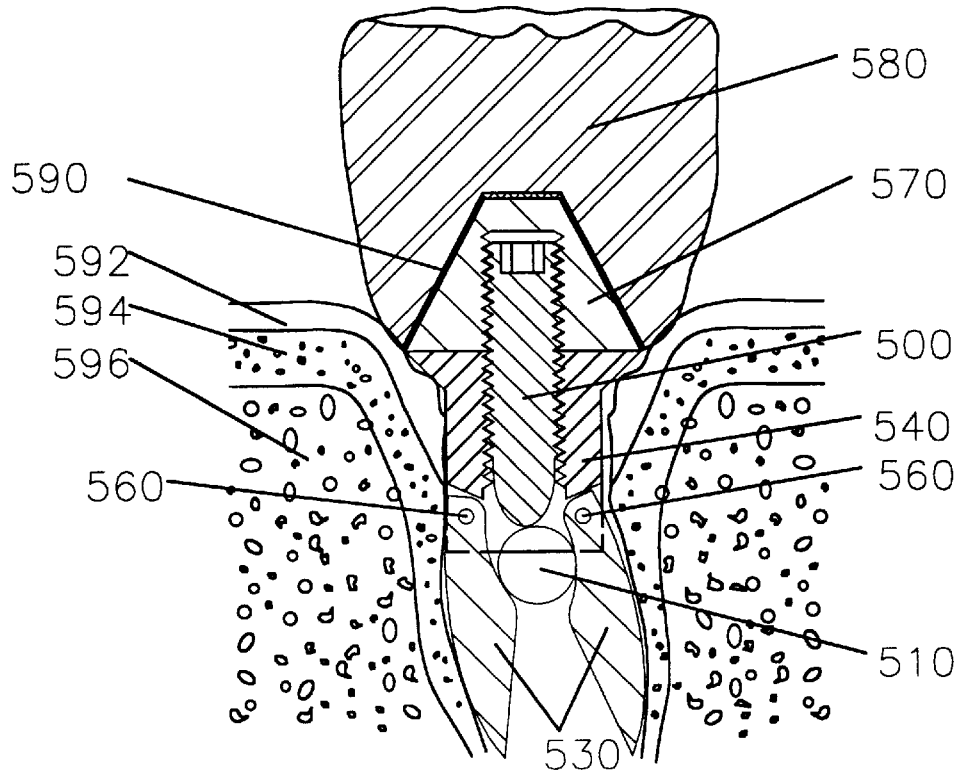
FIG. 6a and FIG. 6b provide a cross-sectional plane view of a fastener with pinned members, and sphere and shaft actuator mechanism configured as a dental implant. The dental implant is shown in bone with in-phase (FIG. 6b) and out-of-phase (FIG. 6a) member expansion.
Figure 6B:
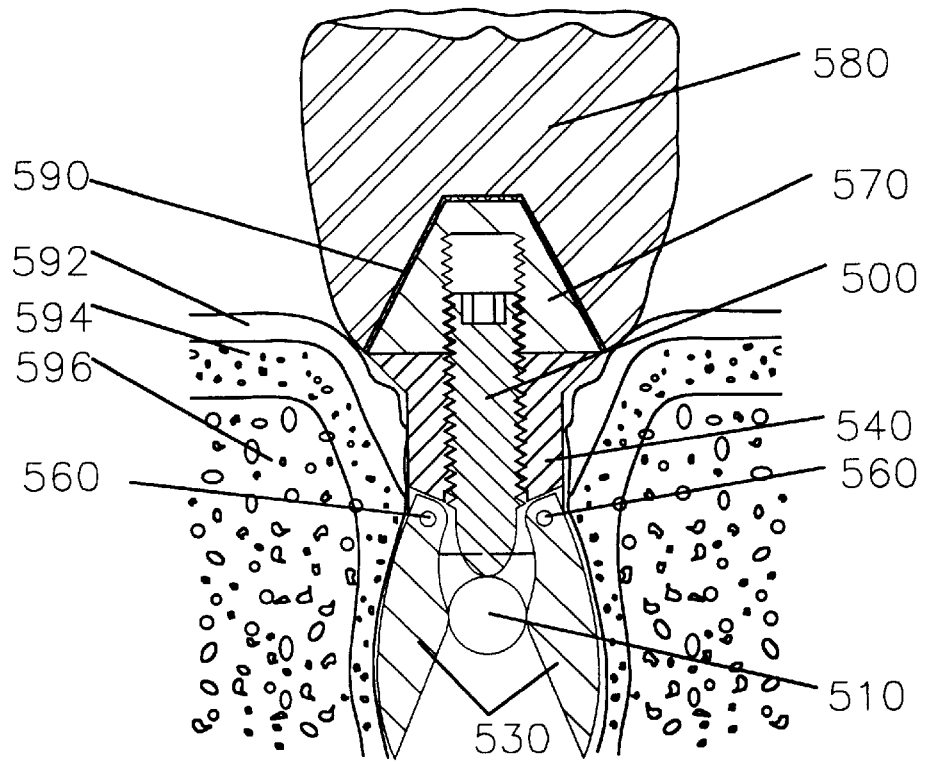
Figure 7A:
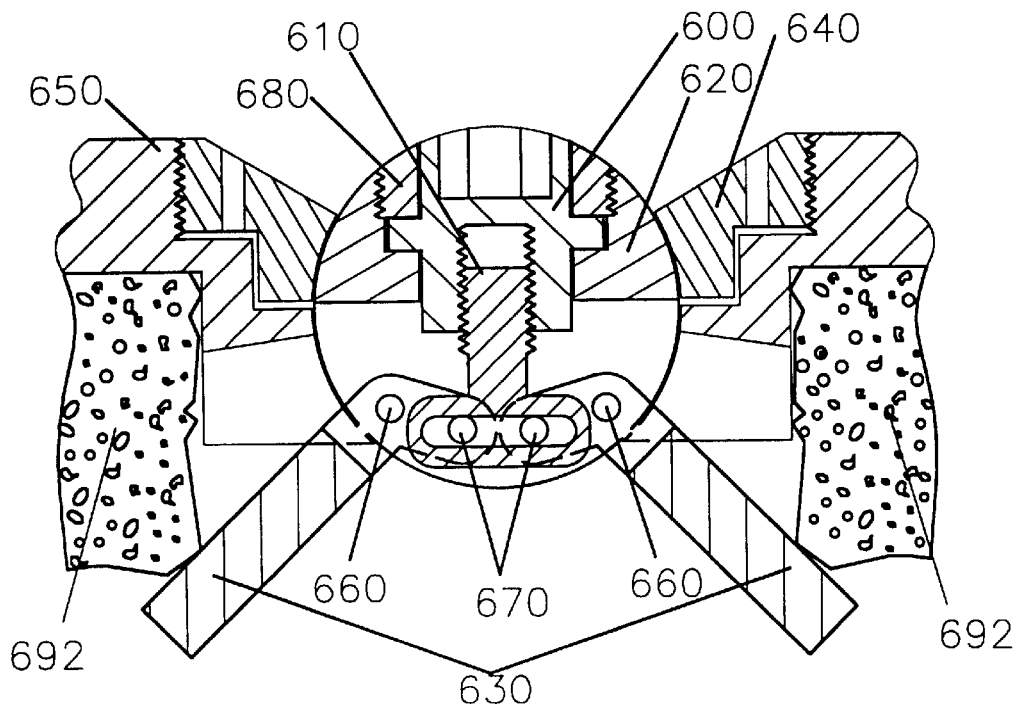
FIG. 7a and FIG. 7b provide a cross-sectional plane view of a fastener with a member mechanism in a spherical rotating housing configured in a plate that allows rotation. The plate is held to the bone surface by the fastener.
Figure 7B:
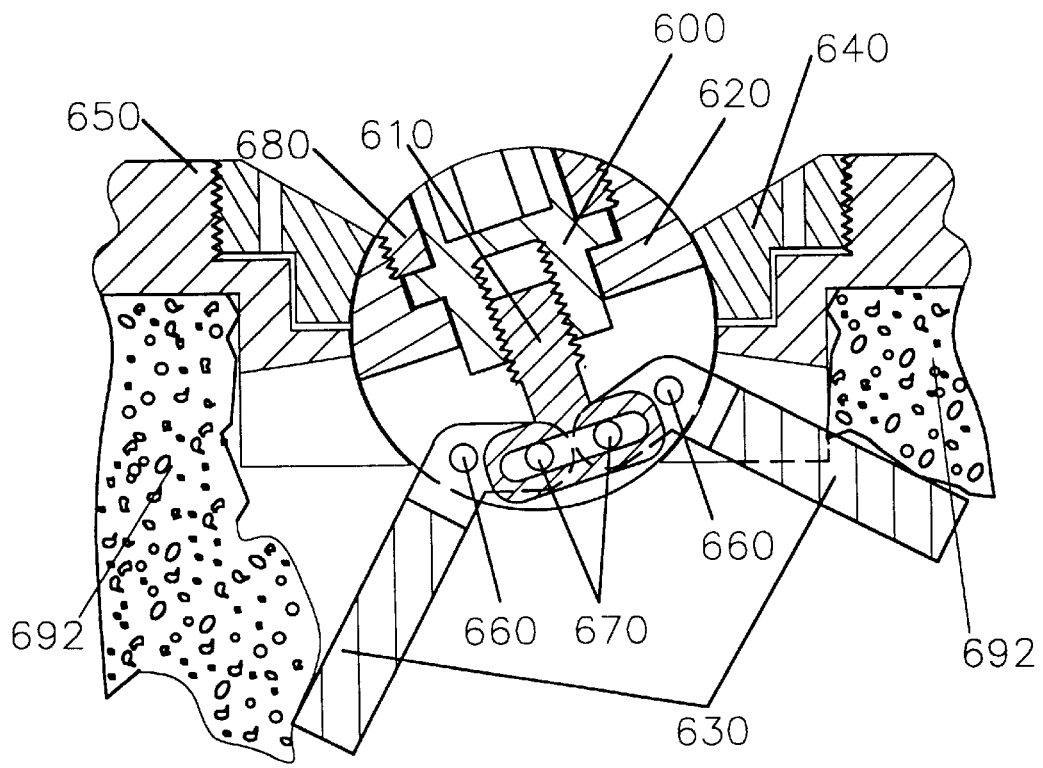
Figure 8A:
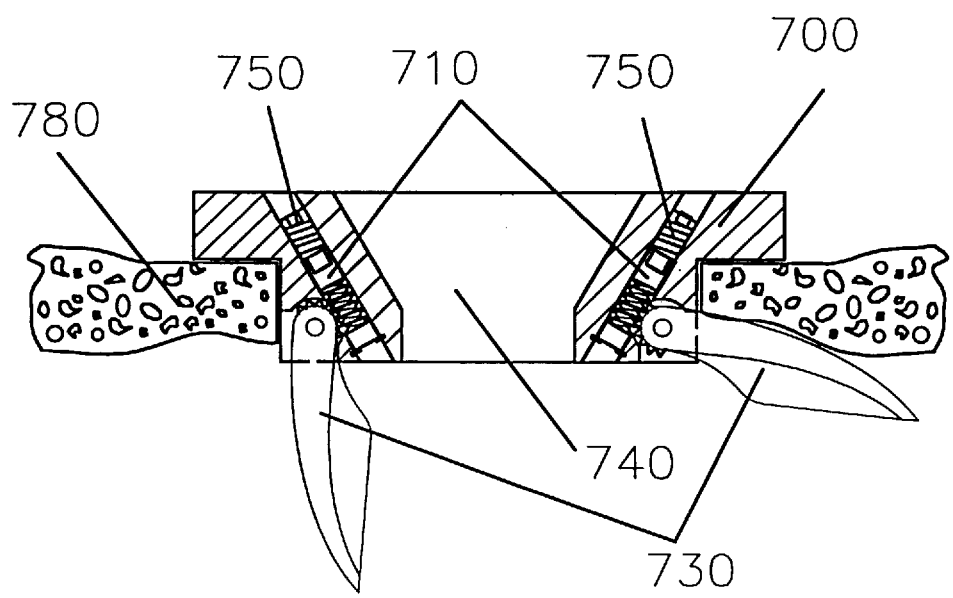
FIG. 8a and FIG. 8b provide a cross-sectional plane view of a fastener having a conformal mechanism including members with worm gears and pinions. A cross-sectional plane view magnified to illustrate the member's worm gear and pinion is shown in FIG. 8b.
Figure 8B:
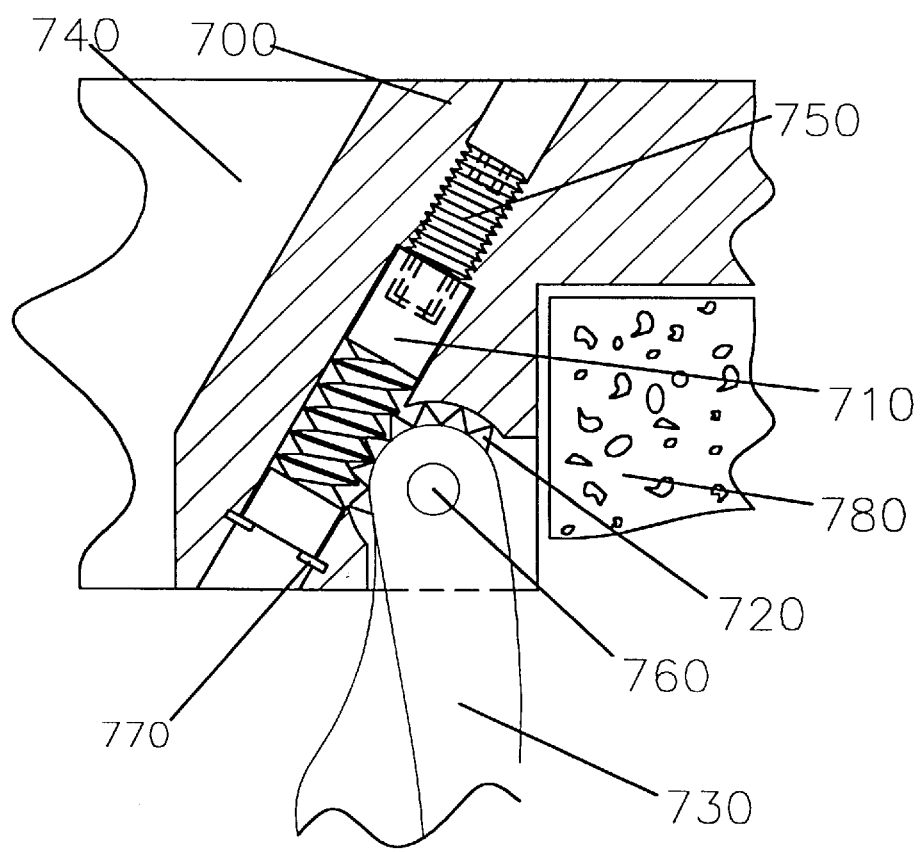
Figure 25:
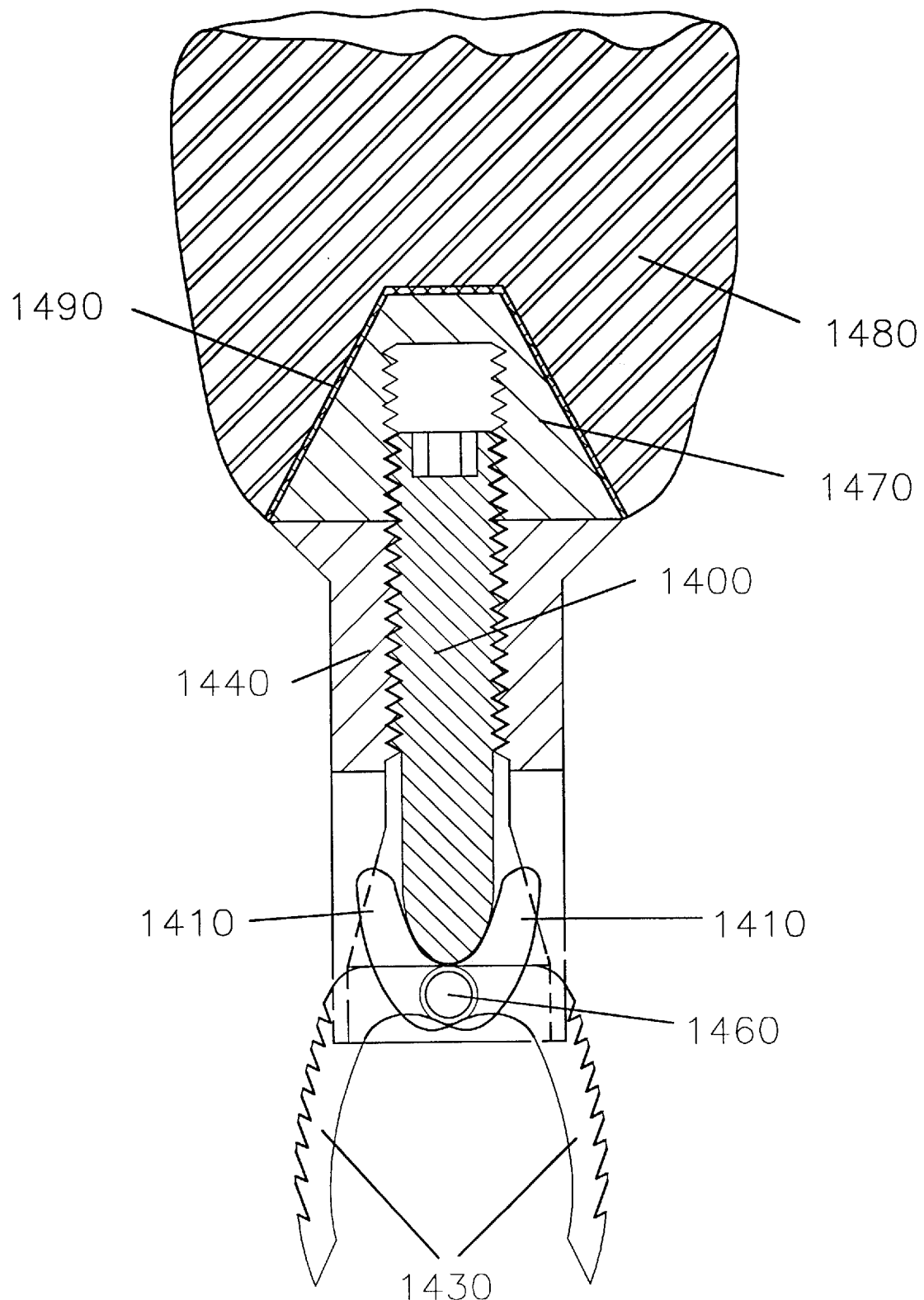
FIG. 25 shows a cross-sectional plane view of a fastener where the sphere 420 of FIG. 5 has been removed; in the present embodiment, the members are movable in a coordinated self-seeking dependent fashion.

Fastener having Shaft-Member Arm Actuator Mechanism for Dependent Movement of Members: In FIG. 25, the fastener of FIG. 5 has been reconfigured for dependent movement of members (1430) by removing sphere (420) of FIG. 5, and reshaping arms (1410) at the point of sliding contact with the actuator (1400).

Figure 26:
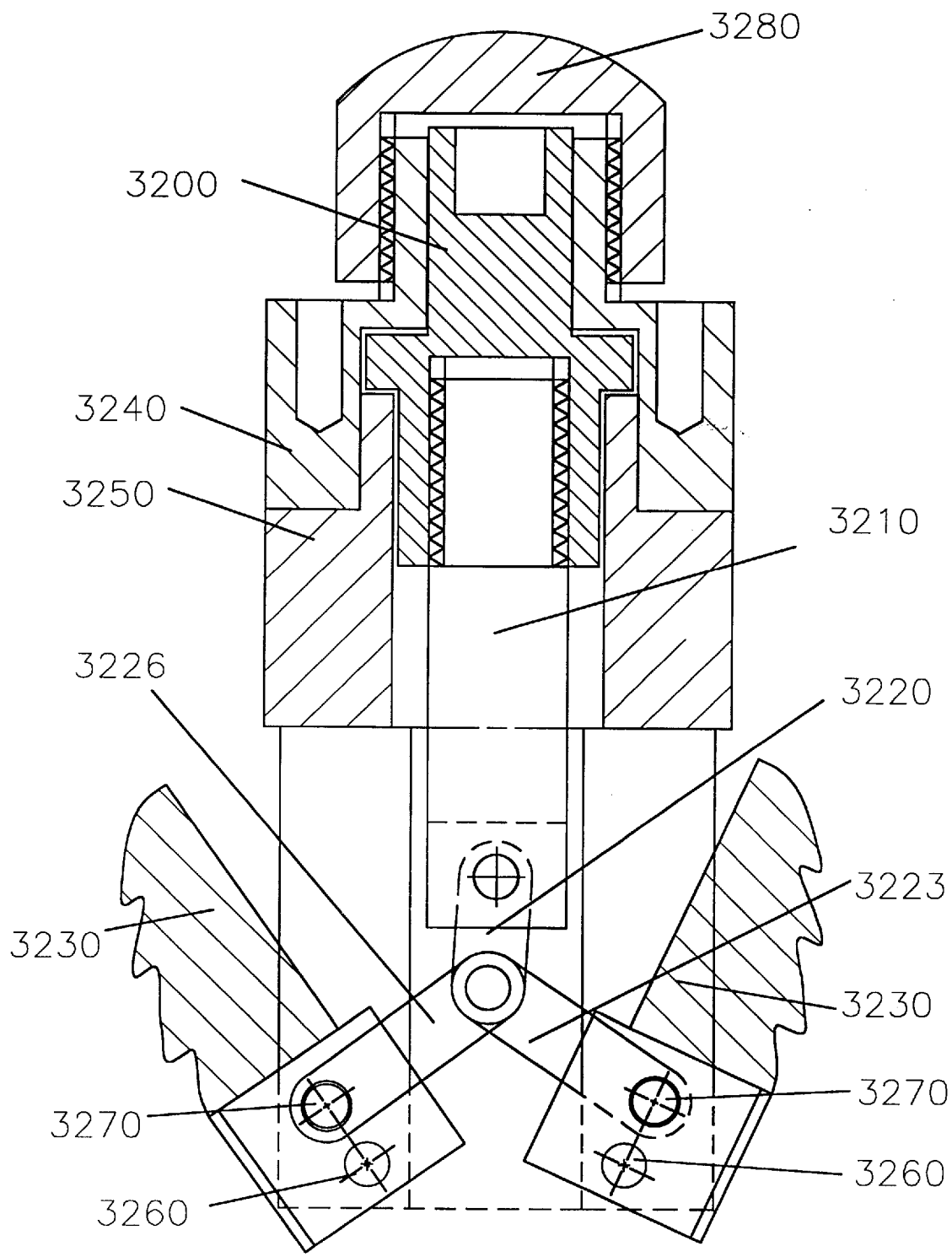
FIG. 26 shows a cross-sectional plane view of a fastener as shown in FIG. 3 modified such that the member orientation with respect to the actuator is reversed so as to allow the members to swing out from the top of the body.

Fastener having Members Movable from the Top rather than the Bottom of the Device: In FIG. 26, the fastener of FIG. 3 has been reconfigured to demonstrate that any of the fasteners provided herein could be configured so that members (3230) pivot to swing out from the top instead of the bottom of the device.

A method of implanting a fastener of the present invention into a hard tissue defect includes the following steps: i) obtaining an animal in need of a fastener of the present invention, ii) determining size of an already existing hard tissue defect, or constructing a hard tissue defect and determining its size, iii) selecting a fastener having a size to fit in the defect and taking into account considerations of defect geometry whether the members will contact the walls of the defect or reach through the defect so as to extend into a cavity, and the relationship between interfacial pressure and actuation force and the strength of the critical components, iv) placing the fastener into the hard tissue defect, v) applying force to the fastener using a tool that applies force sufficient to secure the device and stimulate bone to become more dense. The method may optionally include vi) placing a healing cap over the fastener, or placing a prosthesis onto the fastener.

Figure 2:
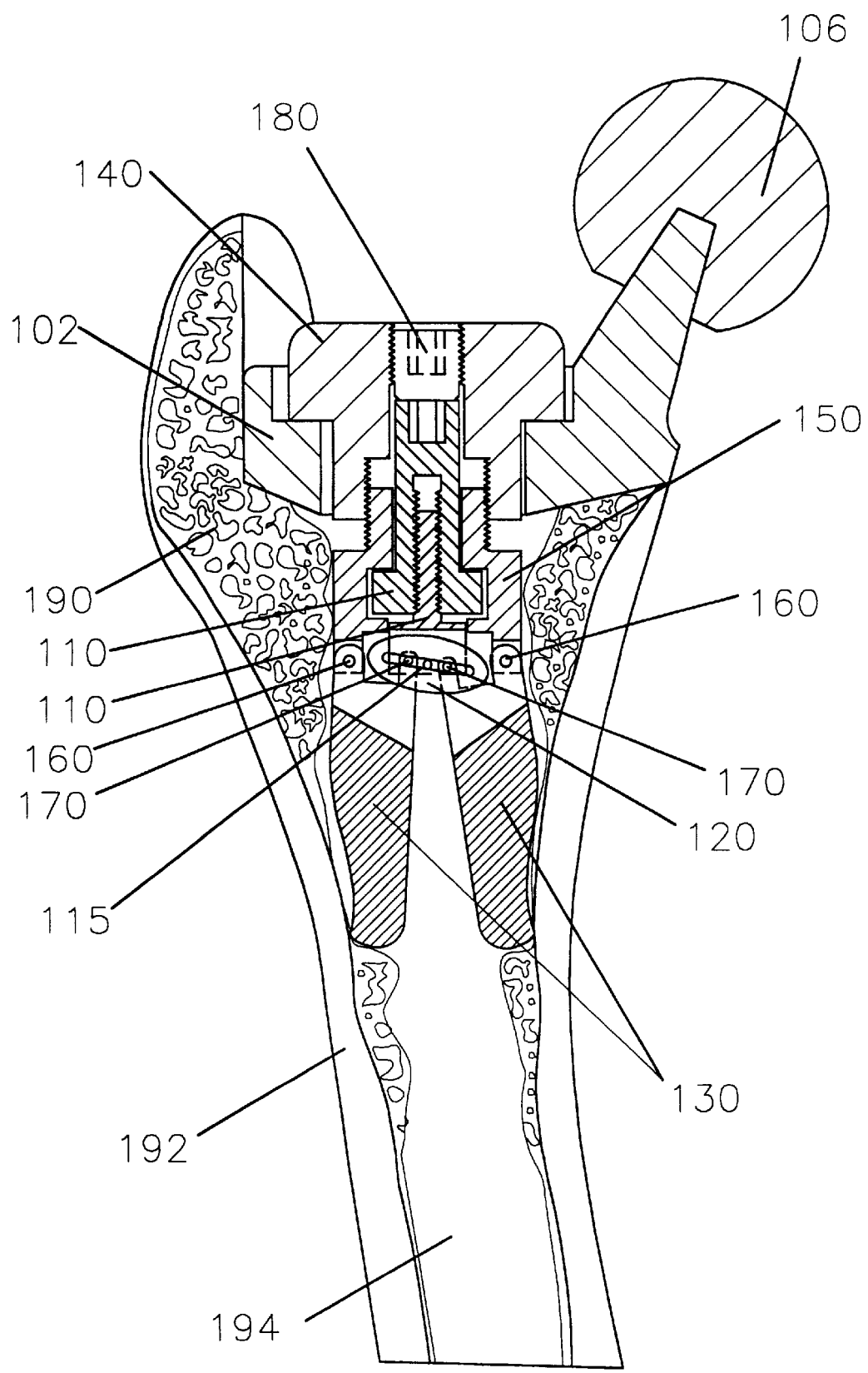
FIG. 2 is a cross-sectional plane view of a fastener having a cammed-member mechanism configured and shown as a femoral component of a hip prosthesis.

A method for determining interfacial pressure exerted on bone surrounding an implanted fastener of the present invention includes the steps of: i) applying force to the implanted fastener using a tool where the force can be measured, ii) measuring the extent of journal translation, iii) measuring index member angle, iv) measuring reference member angle, v) determining interfacial pressure from the equation provided in FIG. 11 for the device of FIG. 2. Similar equations can be derived for the other mechanism configurations in light of the teachings of the present disclosure. In the case of dependent movement, the index and reference member angles are equal.

Fasteners of the present invention may be machined and assembled by one of skill in the art in light of the teachings of the present disclosure. Methods of use of a fastener of the present invention are also known to one of skill in the art in light of the teachings of the present disclosure.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following example is included to demonstrate a preferred embodiment of the invention. It should be appreciated by those of skill in the art that the techniques disclosed in the example represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

In vivo Dental Implant Fastener and Evaluation Thereof

The present example provides an evaluation of an endosseous (bone contacting) dental implant of the present invention. Devices were designed to be placed through the gingiva into a tooth extraction site, expand, conform to the defect and become immediately stable.

Figure 9B:
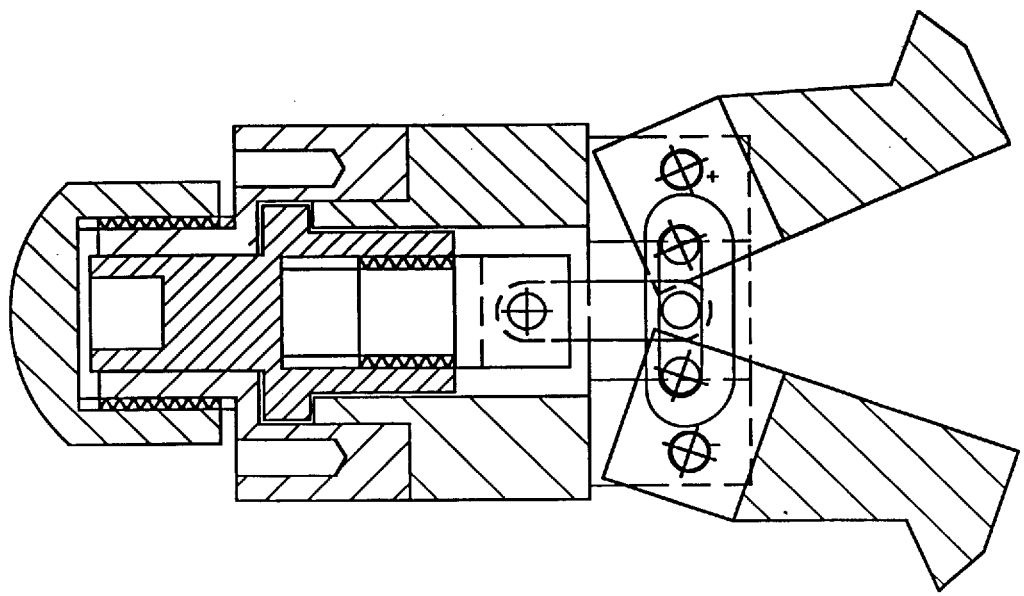
FIG. 9a and FIG. 9b provide mechanical drawings of the implant fastener used in Example 1.
Figure 9A:
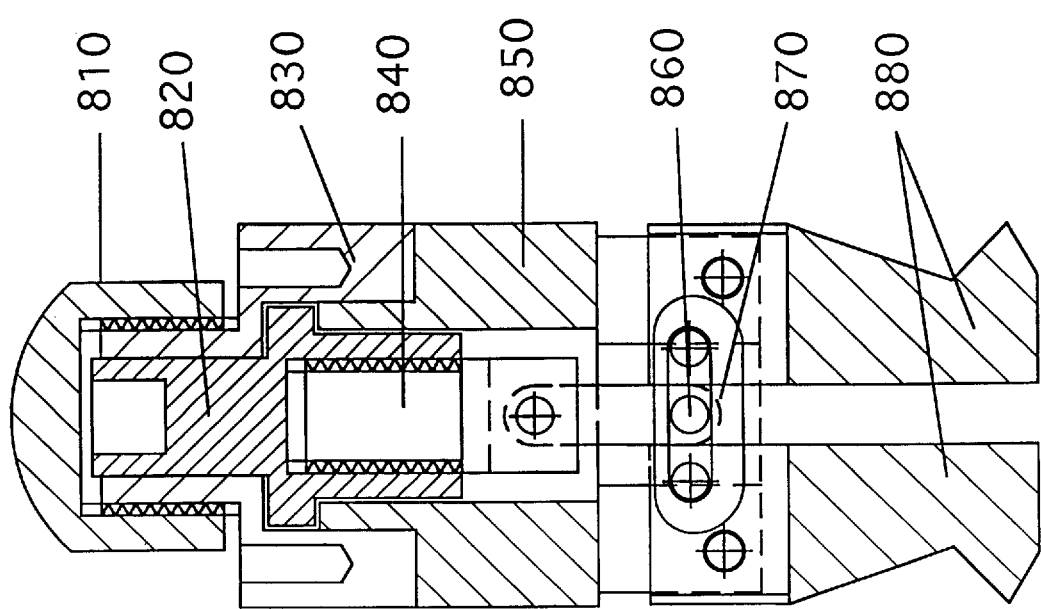

The design used the cammed linkage system to independently expand a pair of members (FIG. 9a, FIG. 9b and FIG. 2; the reference numerals for FIG. 9a are: 810, healing cap; 820, actuator nut; 830, upper body; 840, actuator mandrel; 850, lower body; 860, actuator-cam pin; 870, cam; 880, member). The design used two cylinders that are press-fit together to hold the bearing and journal, and to form the body of the fastener. Two pinned members rotate about two tabs that protrude from the lower face of the body. The members are pinned with the journal in the cam slot, allowing the journal and member pins to slide independently. The upper end of the journal is threaded into the actuator bearing. Rotation of the bearing by applying force to the installation instrument causes the journal to move downward and engage the members through the cam. The fasteners may further include a healing cap driver, an actuator driver, anti-rotation spanner.

The methods used to evaluate the fasteners of the present invention addressed three broad topics: engineering design, engineering evaluation, and in vivo and explant evaluation.

Engineering design for the cammed-member mechanism involved the determination of the appropriate size and shape for the experimental animal, its range of member motion and expansion, its extent of out-of-phase member operation, component interference, the strength of its critical components, a method to lock the mechanism, and its bone-implant interfacial pressure as a function of mechanism engagement torque.

Requirements for size, shape and extent of expansion of both implant designs were determined through the evaluation of fresh dog mandibles provided through the experimental surgery teaching program at the University of Texas Health Science Center, (San Antonio, Tex.). Mandibles were cut in the mesial-distal and buccal-lingual planes. The mesial root of the first molar was selected as the first site for investigation. This selection provided size and shape information for implant design. The strength characteristic of the necropsy specimens provided an estimate of the extent of expansion required for the two implant designs.

The extent of member motion, out-of-phase operation and expansion for the cammed-member implant required the detailed design of all components. The body size and shape, mechanism's pin diameters, cam slot and overall length, member arm length, actuator-translation distance, and actuator-nut rotation versus translation relationship all effect the operation of the mechanism.

A computer design simulation for the member implant was developed using MATHCAD™ to account for and understand the large number of deign variables. This simulation allows the selection of all design variables, solved a system of equations, computed the operational range of the mechanism, and provided a graphical layout of the mechanism to check for component interference. This simulation allows rapid design assessment of operational parameters and is well suited to support the resizing and optimization of the member implant system.

Critical mechanism component strength was performed using conventional machine design theory. The critical components were determined to be the actuator-cam pin, actuator journal bearing and nut, and cam (FIG. 9a, FIG. 9b, and FIG. 2).

Actuator-cam pin: The standard method of determining the maximum force supportable by a clevis-pin arrangement as found in the present implant fasteners is the double lap shear equation (Shigley, J. E., *Mechanical Engineering Design*, 3rd ed., Holman, J. P., ed., McGraw-Hill Book Co., 1977).

Given values of 60k psi maximum shear (Ti-64) and a pin cross-sectional area of $1.26 \times 10^{-3}$ in$^2$, the calculated maximum force the pin will support before shear yielding occurs is 150.8 lb. A safety factor of 2 should be applied, reducing the maximum expected sustainable load to 75.4 lb. This equates to 8.22 in-lb of torque applied to the actuator (Table 1).

A second, more conservative method of analysis is to consider the pin as a beam with constrained ends and a point load applied at the center. For such a beam, the force required to initiate yielding is governed by the bending moment at the center of the pin radius and cross-sectional geometry. Using this method, maximum sustainable force is calculated to be 55 lb. This equates to 5.99 in-lb of torque applied to the actuator (Table 1).

Actuator journal bearing: Failure of a power screw type actuator journal can occur in one of two different manners, compression yielding of the entire screw or stripping of the threads. Thread recommendations assume that the screw will fail just before the threads strip. The minimum thread engagement length necessary to prevent stripping of the threads is assumed to be 0.07 in. When the members are deployed in the orientation of maximum screw travel, the remaining thread engagement length is 0.1165 in. With a compressive yield strength of 120k psi (Ti-64), the screw would be able to withstand a compressive load of 996 lb. This equates to 109 in-lb of torque applied to the actuator (Table 1).

Cam: The upper section of the cam with a thickness of 0.035 inches was modeled as a simply supported beam with a moment applied at each end. For such a beam, the force required to initiate yielding is governed by the moment produced at the center of the beam, ½ the height of the beam and the second moment of inertia. For the upper and weaker section of the CAM, the maximum sustainable force is calculated to be 52.8 lb. This equates to 5.75 in-lb of torque applied to the bearing. The lower section of the cam with a thickness of 0.06 inches was modeled as a simply supported beam. The maximum sustainable force for the lower beam is calculated to be 114 lb. to 12.41 in-lb of torque applied to the bearing (Table 1).

TABLE 1

Maximum sustainable forces for critical components.

| Component | Maximum Force (lb) |
| --- | --- |
| Cam | |
| Upper Beam | 52.8 |
| Lower Beam | 114.0 |
| Bearing and journal | 996.0 |
| Actuator-cam pin | |
| Double Lap Shear Method | 75.4 |
| Beam Method | 55.0 |

Using the beam method, the cam pin, and the upper portion of the cam can be considered the critical members and equivalent, given the assumptions used for the analysis. A sustainable force of 52.8 lb equates to 5.75 in-lb of torque applied to the journal. The Vident IMPAC torque wrench chosen to tighten the member implant fastener can deliver a maximum of 2.83 in-lb (32 Ncm) of torque. This allows a safety factor of 2.0 for the mechanism.

Mechanism locking and bacterial sealing is accomplished through interference of the healing cap 810, 280 or prosthesis abutment 470, 570 and the actuator nut 820. The cap 810, 280 or abutment 470, 570, when installed, jam against the actuator nut 820 causing it to bind against the internal aspects of the mechanism body. This creates three metal-to-metal bacterial seals. One is between the cap and the body, a second between the actuator nut and the internal face of the cap, and the third between the lip of the actuator nut and the internal lip of the body. These three seal faces minimize the likelihood of bacterial migration through the implant mechanism.

Figure 10:
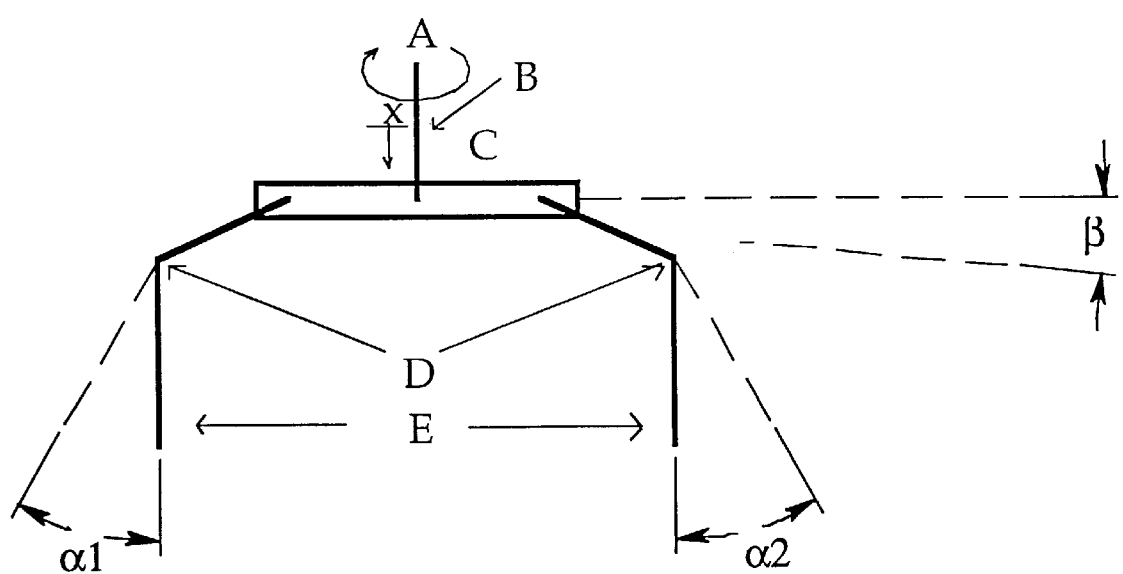
FIG. 10 shows the implant fasteners of the present invention reduced to a simplified model having the following parameters: A, Torque; B, Actuator (Power Screw); C, Cam; D, Fixed Axis of Rotation; E, Members; α1, Index member; α2, Reference Member; β, Cam angle.

Bone-implant interfacial pressure is a function of the torque applied to the bearing nut during the placement of the implant (FIG. 10). The pressure applied to the implant-bone interface can be determined by examination of the mechanism. The design used in this study allowed the implant members to rotate from $-10^{20}$ to 57.5° (positive is out and negative is in towards the centerline). This mechanism allows the members to operate independently and 37.5 degrees out-of-phase from one another. The interfacial pressure applied to the bone interface can be measured by relating the force applied by the power screw (bearing and journal) to the cam and members.

In operation, turning the bearing applies a force to the cam which, in turn, causes the members to rotate outward. It is convenient for the purpose of this analysis to treat this as two separate functions. The actuator screw can be analyzed as a power screw turning against a load and the cam and members as a simple three bar mechanism.

The position of the cam and second member are computed if the position of one member is known. This known position is equivalent to bone contact of one member while the journal is translated and the second member is still moving. The rotation of the cam (β Cam-Angle), given a restrained-member angle (α-index), and extent of journal translation (ΔX) is computed as shown in FIG. 11. The analysis of the power screw is a straightforward application of the equation given in "Mechanical Engineering Design", Shigley and Mischke, (as cited herein) and shown in FIG. 11, with known values particular to the present implant fasteners.

Using simple geometric principals and an understanding of the forces applied to the members the interfacial pressure value can be obtained.

Figure 12:
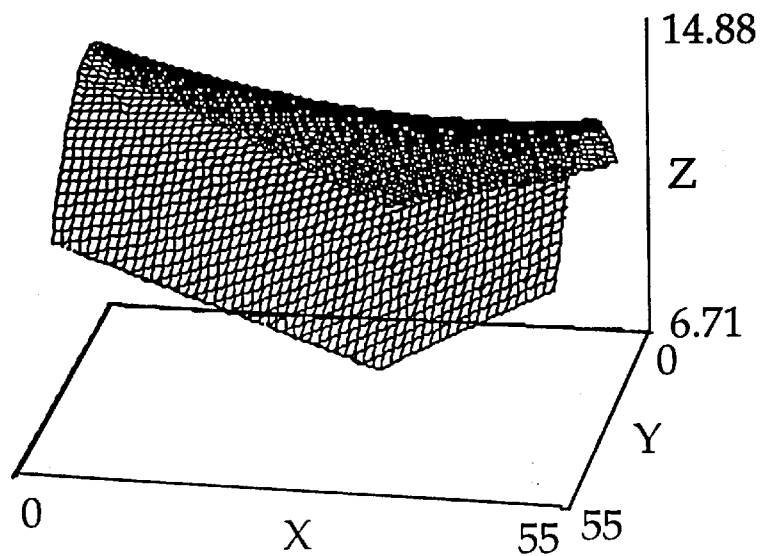
FIG. 12 provides a graph of torque to pressure multiplier (Z) versus member orientation; reference member angle (deg) (Y), and index member angle (deg) (X).

The equation of FIG. 11 has three degrees-of-freedom: torque, index member angle, and reference member angle. To generate the torque-pressure multiplier surface, the reference member is swept through its full range of motion, then the index member is advanced 1° and again the reference member is swept. This algorithm is continued for the range of the index member. The result is the torque-pressure multiplier surface shown in FIG. 12. A new surface is created for each new value of applied torque and each design (size) of the implant. The surface in FIG. 18 represents an applied torque of 1 in-lb.

Figure 18:
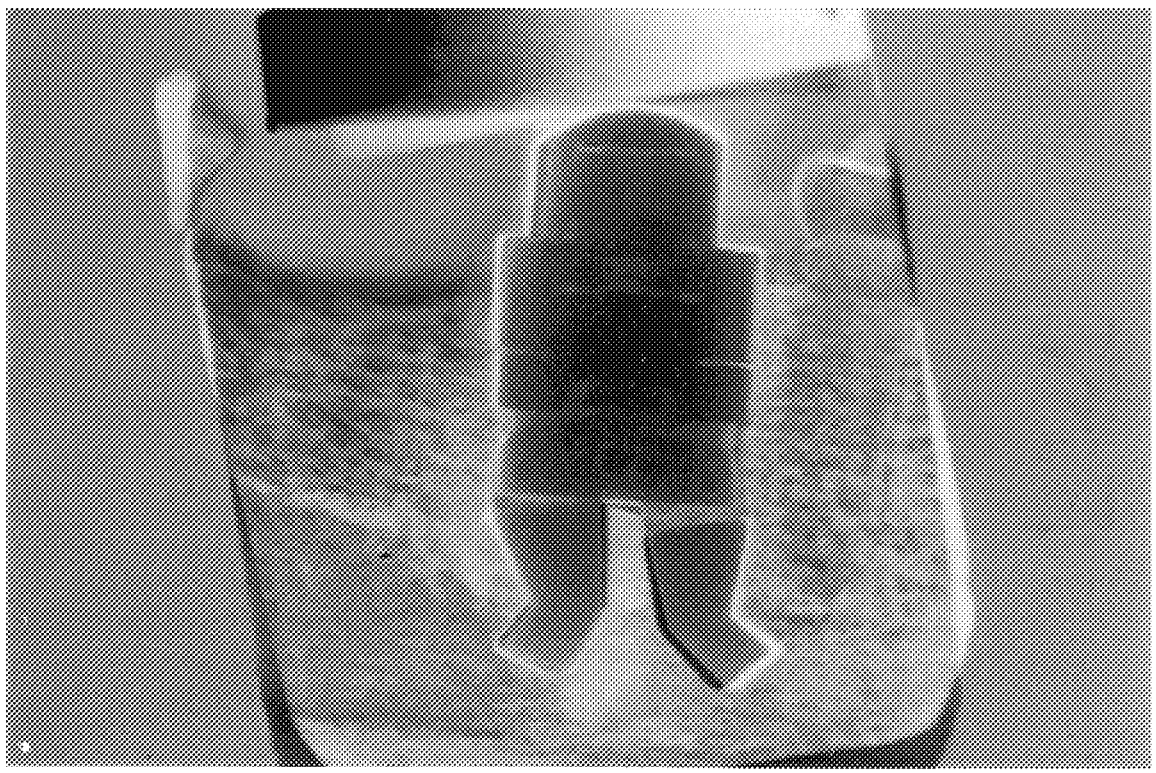
FIG. 18 provides results from dual subtraction radiographs of a member fastener showing filling of the extraction site void between the members and below the implant and an increase in bone density adjacent to the members due to forces exerted by the members on the surrounding bone. Increases in bone mineral density is seen in light regions and decreases in dark regions.

From the graph of FIG. 18, the orientation corresponding to the maximum (index angle=0°, reference angle=16°) and minimum (index angle=34°, reference angle=55°) multiplying effect can be found. To calculate the pressure (psi) on the reference member, the multiplier value associated with a particular set of member angles is multiplied by the torque applied to the implant. Taking these minimum and maximum torque-to-pressure multiplication values as boundaries and varying the torque from 0 to 9 in-lb (implant hinge pins fail at 6 in-lb to 8.22 in-lb), an envelope of implant interfacial pressure as a function of torque can be plotted as shown in FIG. 13.

Figure 13:
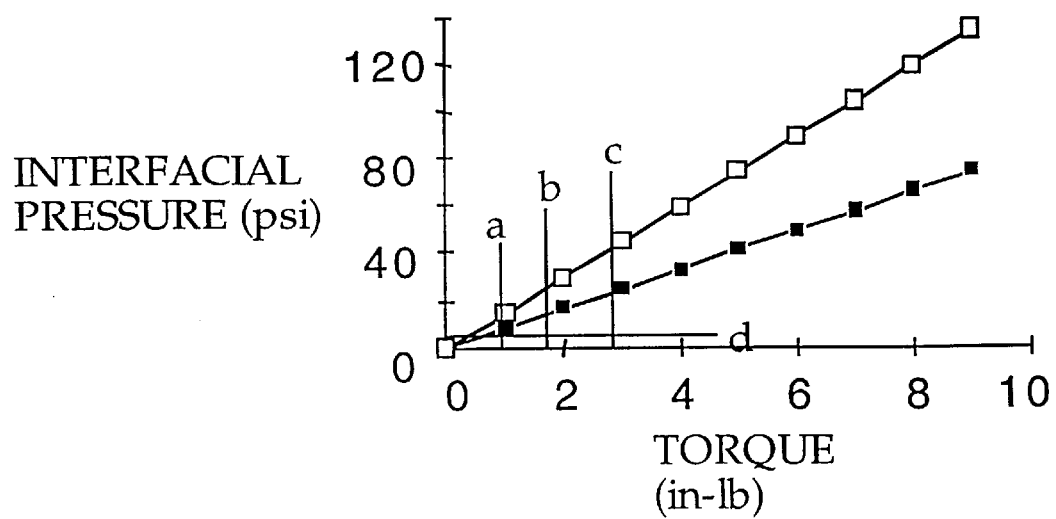
FIG. 13 provides a plot of pressure vs. torque as a function of pressure multiplier: a, 10 Ncm; b, 20 Ncm; c, 32 Ncm; d, 300 mm Hg; □, maximum multiplier; ■, minimum multiplier.

IMPAC torque wrench (Vident) values of 10, 20 and 32 Ncm and an oscillometric method blood pressure monitor cuff release pressure of 300 mmHg are shown in FIG. 13 for reference. If the implant will fail at the journal-cam pin at 8.22 in-lb applied torque, a safety factor of over three exists for a bearing torque of 32 Ncm.

Instruments for manipulating the implant fastener included an anti-rotation wrench, a bearing driver, or a healing cap driver. The anti-rotation wrench is a two-pin spanner. The pins of the spanner engage two holes on the upper face of the body of the implant. The spanner can be fastened to the body of the implant with the healing cap to facilitate handling of the implant during placement. The bearing driver has a male toroid shaped end. This end fits the female socket in the bearing. Rotation of the driver turns the bearing and operates the mechanism. The healing cap driver is a toroid shaped socket driver used to place and remove the healing cap.

Mechanical testing of the pull-out resistance of dental implants was performed for the cammed member, wire-cage and conventional Nobelpharma implant designs. The bone contacting portion of each of these implant designs was embedded in paraffin and pull-in tension to determine the intrinsic resistance of the implant to being pulled from bone. The wirecage and cammed-member implants were tested in a dosed and expanded configuration. The Nobelpharma 3.5 mm×20 mm implant was selected for comparison testing because it is the largest and most clinically successful endosseous implant on the market.

Figure 14:
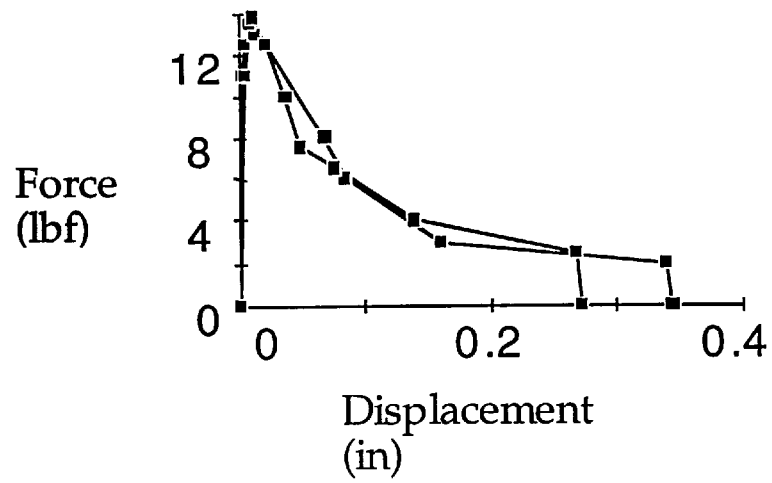
FIG. 14 provides a plot of the force versus displacement curve for the fastener of Example 1 with the members disengaged (closed). Maximum strength - 13.75 lb. Total energy - 1.76 in-lb.
Figure 15:
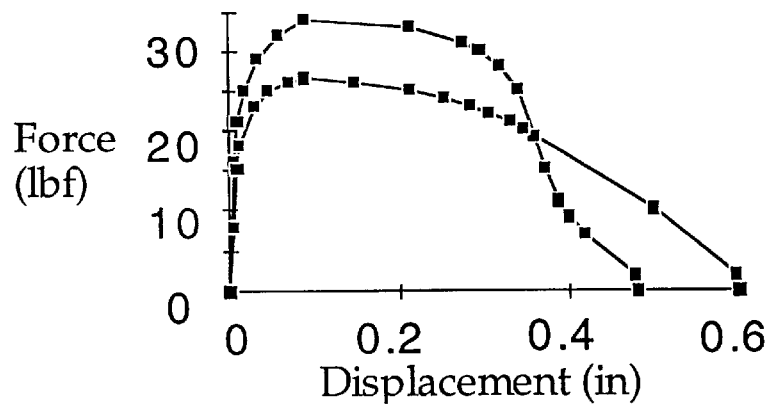
FIG. 15 provides a plot of the force versus displacement curve for the fastener of Example 1 with the members 75% engaged (¾ open). Maximum strength - 34 lb. Total energy - 12.21 in-lb.
Figure 16:
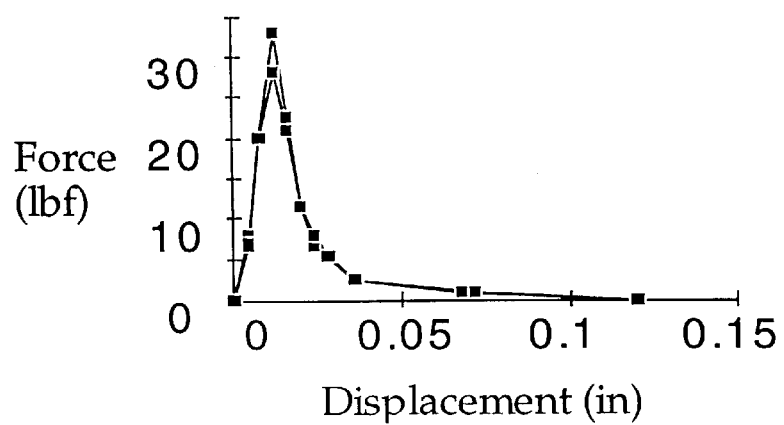
FIG. 16 provides a plot of the force versus displacement curve for the Nobelpharma endosseous 20 mm×3.5 mm screw thread implant. Two tests were performed to determine repeatability of the method. Maximum strength - 28 lb. Total energy - 0.66 in-lb.

Instron model 1127 with a 1000 lb load cell and analog control system was used for these tests. The implant was tested in two configurations, with member closed and member ¾ open. The Nobelpharma implant was tested as delivered. Load (lb) - deflection (in) curves demonstrated that more work (area under the curve) was required to remove the implant fasteners of the present invention in comparison to the Nobelpharma implant (FIG. 14, FIG. 15, and FIG. 16).

Figure 17:
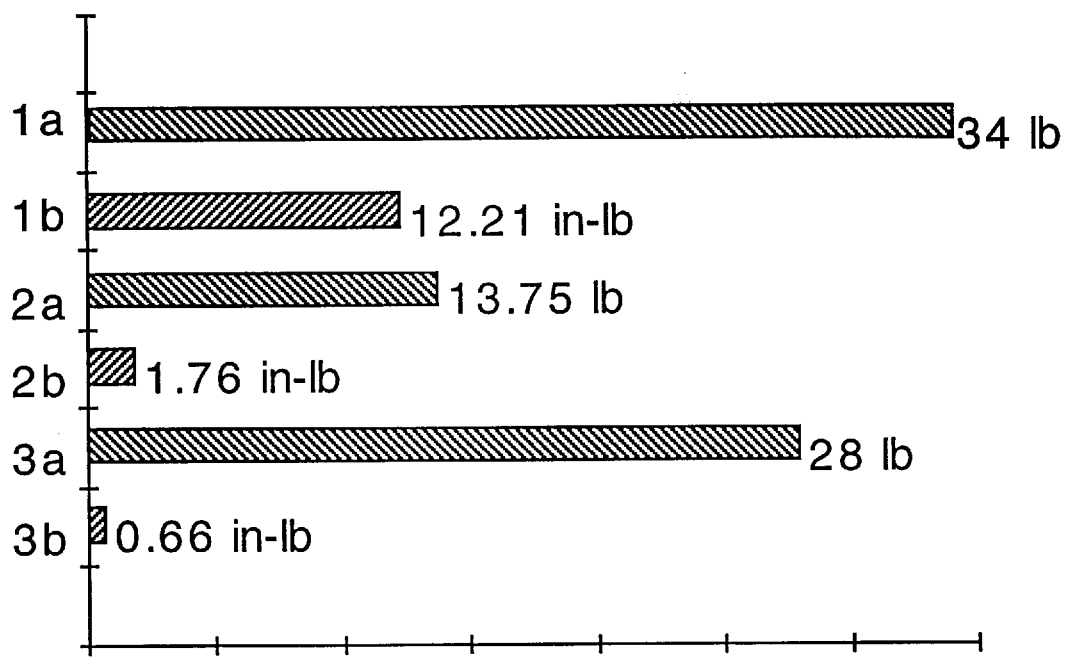
FIG. 17 provides a histogram of combined maximum strength (hatched bar, \\\\\\) and total energy (hatched bar, //////) for different designs and configurations of the fastener of the present invention as compared to the Nobelpharma implant: 1a and 1b, Example 1 fastener, Member ¾ Open; 2a and 2b, Example 1 fastener Member Closed; 3a and 3b, Nobelpharma implant.

The maximum value of the pull-out strength was taken from the graphs. The area under the force-displacement curves were measured. This area is a measure of the work (energy) required to extract the implant from wax. Work and pull-out yield strength for the three different implants were compared in a histogram given in FIG. 17.

All of the implant configurations produced comparable maximum strength values (crosshatched bar). Conversely, the total energy (solid bar) required to completely remove the implant from the wax was significantly greater in the systems of the present invention. This suggests that the implant fasteners of the present invention perform with greater mechanical toughness, resisting pull-out even after failure of the implant-material interface has been initiated.

In vivo evaluations were performed under AAALAC Protocol #92077-11-01-B2 by placing two implants into mandibular first molar extraction sites in heartworm-free dogs following tooth extraction. Teeth were sectioned and extracted. Gingiva was closed around the implant leaving the healing cap exposed. Implant sites were swabbed with PERIDEX™ during the twice weekly evaluation for implant mobility, gingival inflammation and bleeding.

Clinical and radiographic evaluations were performed pre- and immediately post-implantation as well as at 2, 5, 8 and 12 weeks post-implantation and periodically for one year. Soft tissue adaptation to the device was documented photographically. Implant position and bone density and morphology were determined radiographically. Stability was assessed subjectively. At the end of the 12-week period the mechanism of the cammed-member implant was actuated and found to be tight.

Quantitative digital radiographic image analysis was used to determine the bony changes in and around the implant as described by Ruttimann et al. ("Automated estimation of lesion size", SPIE, *Application of Optical Instrumentation in Medicine XIII* 535:325–330, 1985). A stent was used to hold the x-ray calibration wedge and film. The stent had a calibration wedge imbedded on the occlusal surface which was made of a bone-simulating material which was 25 mm long, 10 mm high and had a ramp of 0–5 mm thickness. The reference wedge was made from a bone-equivalent epoxy resin (Model 450 Bone, Radiation Measurements, Inc., Middleton, Wis.).

The processed radiographs were converted to digitized images in 640×480×8 bits format with pixel size of 60 micrometers. Assessment of the alveolar bone changes were performed with a quantitative digital x-ray image subtraction technique. On the monitor image of the radiograph, an area of interest (AOI) was drawn between the members of the cammed-member implant within the region of the wire cage and adjacent to the body of the implants with trackball driven mouse.

The images were then subtracted and compared to the calibration wedge which provided an estimate of the bone mass changes around the implant and in the apical defect between the members.

Morphometric measurements of the alveolar bone were made using the same standardized radiographs that were made for the quantitative image analysis. Digitized radiographic images magnified eight-fold on the computer monitor with a pixel size of 60 micrometers were analyzed using RADWORKS™ software for distance and area measurements (Dove, RADWORKS™, San Antonio, Tex.). The vertical alveolar bone change was measured from implant collar to the alveolar bone crest at the mesial and distal implant sides. The area of the crestal bone change between the adjacent teeth and the implant was measured by outlining the crestal bone level in the baseline radiograph and follow-up radiographs and calculating the area difference between these outlines.

An oral photograph of an implanted fastener healing cap showed good soft-tissue approximation and closure at 8 weeks following implant placement.

The results of this study demonstrated that increases in bone mineral density could be measured adjacent to and between the members at the point of interfacial pressure. On average, decreases in bone mineral density were noted at the crestal portion of the implant.

Measurements of changes in bone morphology and density of the bone surrounding the member implant were made. Linear measurements of crestal bone height changes were taken relative to the top of the implant. Bone mineral density measurements were taken at the mesial and distal border of the upper, mid and lower (at the member interface with bone) portion of the body and between the members at the apex of the extraction site.

The subtracted image showed increases in bone mine density in light regions and decreases in dark regions (FIG. 18). The members were demonstrated to have increased bone mineral density adjacent to the members and at the apex of the extraction site. This increase in bone density indicated that load applied by the mechanism was physiologic and stimulated bone to form with higher density and strength.

Explant and histologic evaluations were performed on three dogs terminated at 8 weeks post-implant placement and at one year. The left and right sides of the mandibles were separated at the sinphysis and fixed in FORMALIN™ for four weeks. Prior to embedding, the mandibles were sectioned in the mesial-distal plane to reveal the implant embedded in bone.

Figure 19:
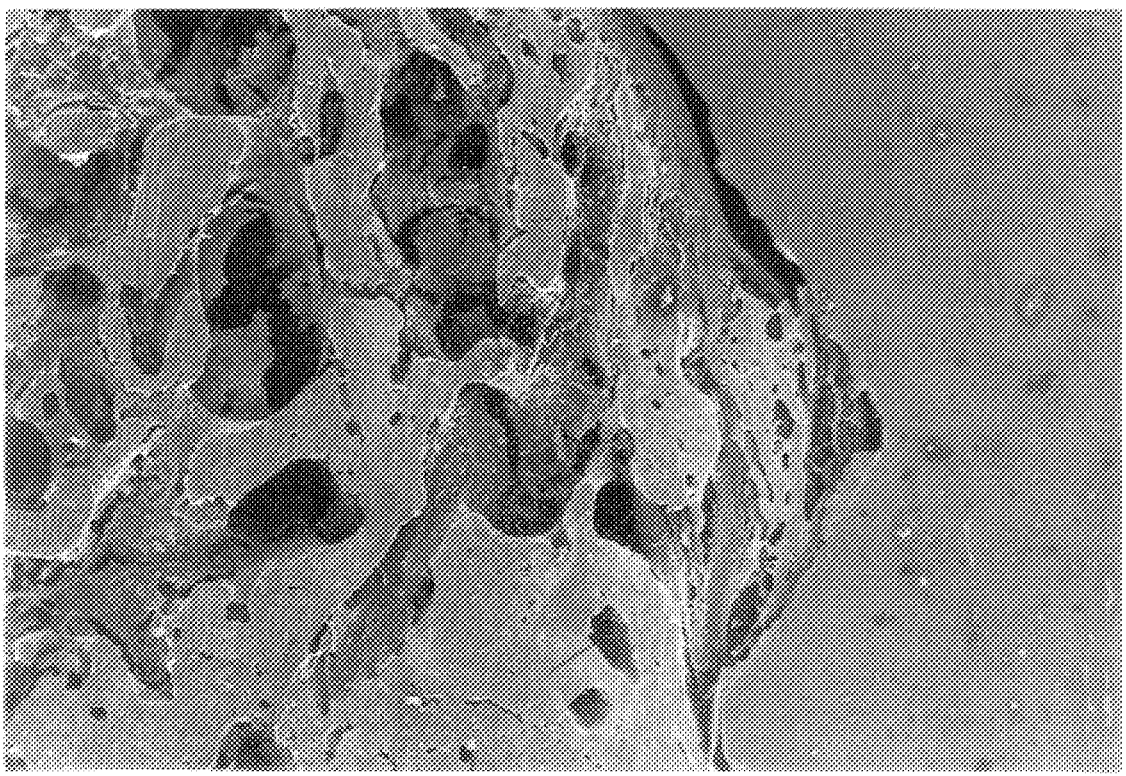
FIG. 19 provides a photograph of the member implant fastener specimen showing dense bone adjacent to the foot of the members.

Four principal assessments were made from gross and scanning electron microscope (SEM) examinations. First, the implant was stable in bone. Second, bone healed around and within the implant in the extraction site defect. Third, force exerted on the surrounding bone caused it to become more dense. Fourth, there was direct implant-to-bone contact (FIG. 19).

Clinical and radiographic evaluations performed over a period of one year showed excellent soft tissue healing and increases in bone mineral density in and around the implant. Subsequent histologic evaluations confirmed the biocompatibility of the devices and the ability of bone to substantially fill the extraction site defect and heal around the implant.

In summary, the principal observations from this study were: 1) the designs were feasible for use in extraction sites and surgically prepared osseous defects; 2) small fastener mechanisms could be built with sufficient strength for application in bone; 3) the implants and instruments supplemented conventional oral surgical practice and may reduce the sensitivity of implant outcome to variation in technique; 4) soft-tissue healed around the crestal portion of the implants; 5) bone healed throughout the defect and within the implant mechanism; 6) the implants were biocompatible and stable in bone following placement and after one year; 7) dual-subtraction techniques were sensitive to changes in bone mineral density adjacent to and within the mechanism of the implants; and 8) the pressure exerted by the member implant increased the density of bone at the implant interface.

EXAMPLE 2

Prosthetic Teeth

Figure 20:
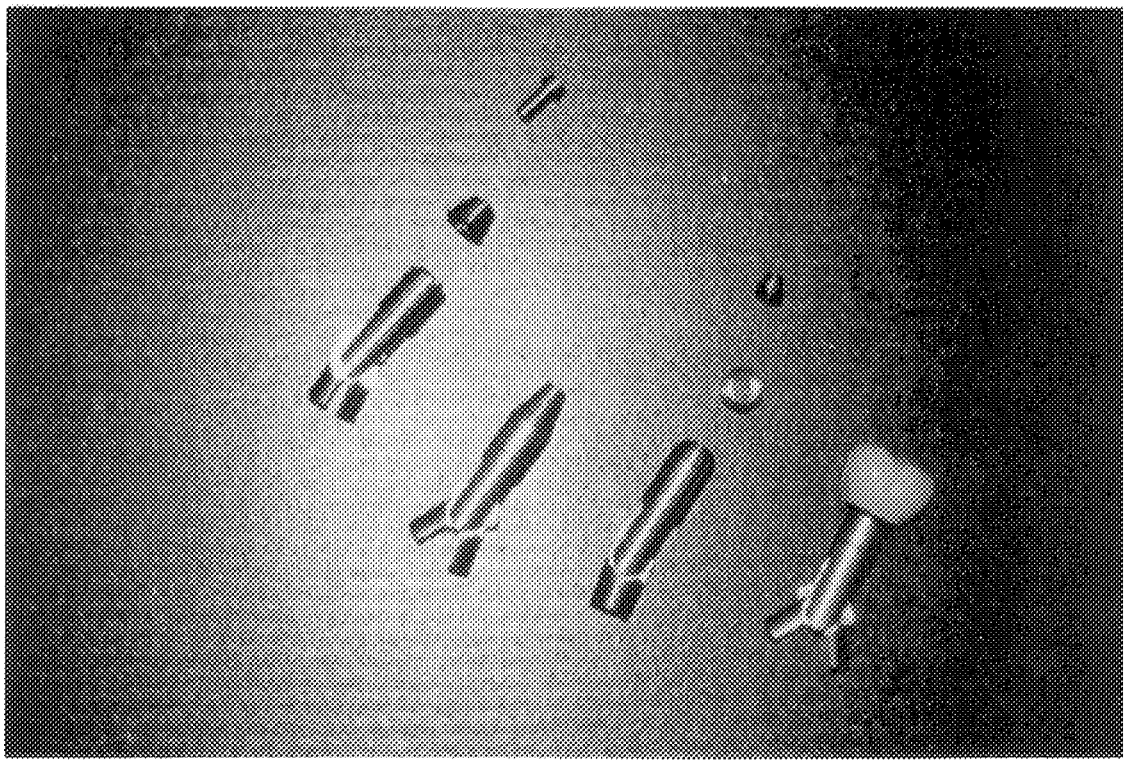
FIG. 20 shows a fastener embodiment configured as a dental implant. Starting from left is the fastener with one member closed and the second partially open demonstrating independent action of the members. The abutment and screw are shown separately above and to the right of the fastener. At center left is the fastener with abutment attached. The members are fully expanded and opened equally. At center right is the fastener with the members together and at an angle to the body showing the ability of the members to adapt to angled defects. The healing cap is attached and a separate healing cap and screw are shown above and to the right. At the far right is a fully expanded fastener with prosthetic human tooth.

Development of the fastener of Example 1 led to the construction of a prosthetic tooth and its testing as a dental implant. The implant fastener structure, healing cap with screw, and abutment with screw have been built and evaluated. Prosthetic teeth have been formed and attached to the structure using the abutment. This embodiment as a dental implant is shown in FIG. 20.

This embodiment is currently implanted in dogs. A nine-month follow-up examination showed that bone surrounding the implant is increasing. None of the devices have failed and the prosthetic teeth are easily placed into position.

EXAMPLE 3

Applications to Orthopaedics

Figure 21:
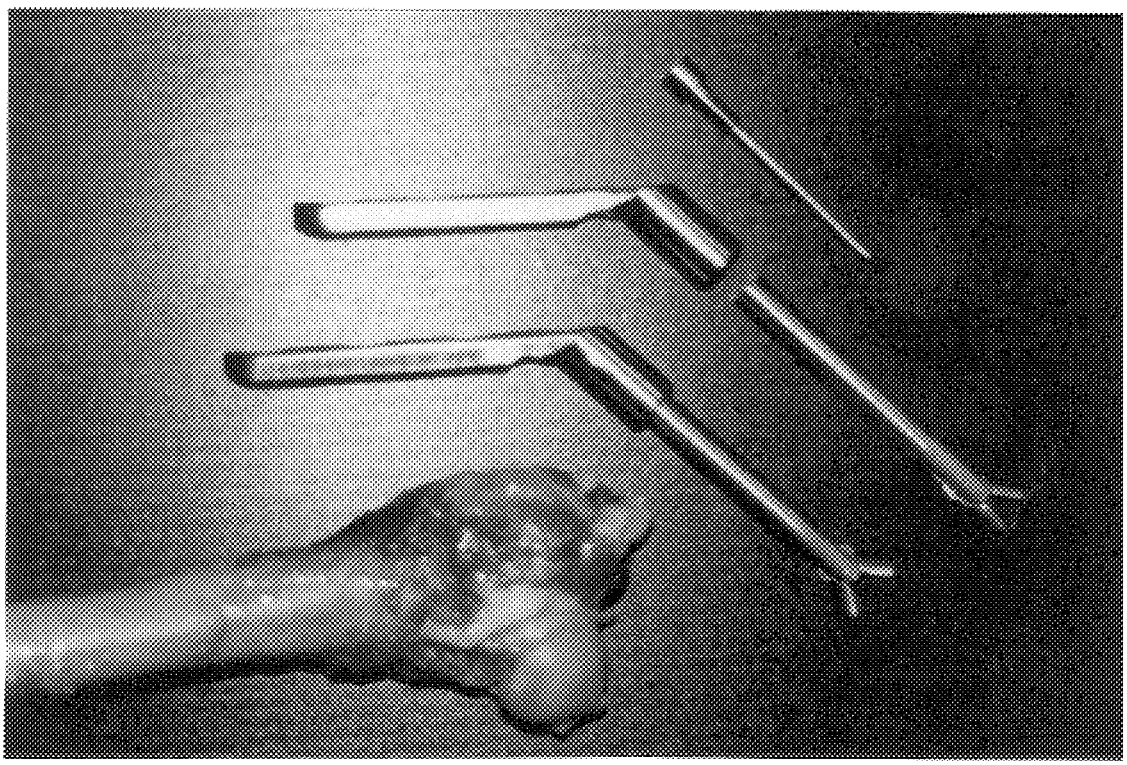
FIG. 21 shows a fastener configured as a femoral neck compression fastener and plate. Starting at the upper right is the plate compression and fixation screw, below it are the plate and an embodiment of the expanding conformal component. Below and adjacent to the dog femur is the assembled femoral compression system.

Further uses of the fasteners of the present invention apply to orthopaedics. A femoral neck compression fastener and plate have been fabricated and are being evaluated in an animal model (FIG. 21). The expanding and conformal aspects of this system are expected to provide significant benefit to patients with femoral neck fractures. These fractures often occur spontaneously in elderly osteoporotic patients. These patients have poor bone quality and conventional femoral neck compression systems, which most often use course screw threads, pull loose due to the poor bone quality. Reports indicate that the failure rate of conventional compression systems is between 40% and 70% (Olerud et al., "Internal Fixation of Femoral Neck Fractures: Two Methods Compared", *J. Bone Joint Surg* [Br] 73-B: 16-9, 1991).

The implant fasteners of the present invention contrast with conventional technology in that the conformal and expanding portion of the subject invention provide an excellent interlock with bone and act to pull the fracture site together so as to facilitate compression across the fracture site and stimulate healing. An additional advantage is that the conformal features of the device minimize the effects of surgical technique with respect to the angle of the hole drilled that is required to be placed into the femoral neck and ball prior to insertion of the device.

EXAMPLE 4

Applications to Industry

The fasteners of the present invention may be used as anchoring, centering, or aligning devices in areas of technologies needing such anchoring, centering, or aligning, especially where such activity is within an irregular cavity, or where irregularities exist in an internal surface. Such areas of technology include water and oil well technology, welding technology, aircraft applications and in automated production, for example.

Fasteners of the present invention may be used for centering, holding and/or aligning various tubular or cylindrical elements for various purposes, such as end-finishing, attachment of other members of various shapes and functions, or centering a holding or clamping mechanism with respect to a tubular member. One problem in welding tubular members together is getting the clamping and guiding structure in proper position for holding the parts while forming the weld, especially where the tubular member has a curved section. Fasteners of the present invention may be useful for aligning and holding such parts, or as a means for guiding a welding unit, especially for automatic or semiautomatic welding.

Alignment of a clamping or holding mechanism in a proper orientation with respect to a plane end surface of a pipe or other tube is a further use of fasteners of the present invention. Further, holding or supporting a special apparatus for positioning, holding and/or welding brackets, arms, special connectors, and the like onto or near the ends of tubular members particularly where accurate positioning and precision holding are essential is a use of the present invention.

Fasteners of the present invention are useful in oil field applications involving fishing tools, for example. In situations of broken or twisted-off drill pipe in a well bore, the downhole pipe must be recovered or the well is lost. The fastening and aligning capabilities of the present fasteners allow the capture and withdrawal of the downhole pipe from the well bore. The fastener would be fixed to the end of a wireline and lowered into the well bore to the level of the broken end of the downhole pipe. The fastener members would be placed in the bore of the downhole pipe. Once engaged, the fastener would be expanded and would lock to the walls of the bore of the pipe, while simultaneously aligning the downhole pipe with the wireline. The fastening and aligning allow a direct and secure pull by the wireline on the downhole pipe so as to lift and allow recovery of the downhole pipe.

Fasteners of the present invention have further utility in aircraft applications where two plates overlap and require joining. In today's fleet of aircraft, mechanical fatigue is causing the riveted joints of the aircraft's aluminum skin to fail. The failure can be avoided by redrilling the rivet hole to remove any cracks and replacing the rivet. Reriveting of the skin can be difficult and expensive. The present invention provides a unique advantage for rejoining the skin panels. Once the old rivet is removed and the hole prepared, a fastener of the present invention can be inserted in the hole and expanded so as to compress the overlapping aluminum skins and form a new and strong union between the skins and airframe.

In a further use of the fasteners of the present invention, various components require aligning in automated production. These production processes vary from assembly to part alignment while running through a conveyor system. In order for wheels, headlight buckets, and other objects to be placed on the frame or body of an automobile, for example, they must be retrieved from stock, held, transported and placed on the automobile. These processes require an adaptive holding and aligning device. Fasteners of the present invention would automatically fasten to a wheel rim and align the rim with the arm of a robot used to place the rim on the axle, for example. This holding and alignment would allow the robot to automatically know the orientation of the wheel so that it could repeatedly place a wheel on an axle.

All of the devices and methods disclosed and claimed herein be made and executed without undue experimentation in light of the present disclosure. While the devices and methods of this invention have been described in terms of preferred embodiments, it will be apparent to those of skill in the art that variations may be applied to the device, methods and in the steps or in the sequence of steps of the method described herein without departing from the concept, spirit and scope of the invention. All similar substitutes and modifications apparent to those skilled in the art are deemed to be within the spirit, scope and concept of the invention as defined by the appended claims.

I claim:

1. A fastener for implanting into a cavity, the fastener comprising:
   a body;
   a plurality of members movably connected to the body, each member being independently movable for coordinated self-seeking conforming to the cavity; and an actuator mechanism for coordinating and translating applied force to each member.

2. The fastener of claim 1 wherein an interfacial pressure exists between each member and the cavity when in use.

3. The fastener of claim 1 wherein the cavity is a hard tissue defect.

4. The fastener of claim 3 wherein a sufficient interfacial pressure exists between each member and the cavity to cause hard tissue density to increase when in use.

5. The fastener of claim 3 further comprising a prosthesis connected to the fastener.

6. The fastener of claim 1 wherein the actuator mechanism further comprises a locking mechanism for locking the actuator mechanism.

7. The fastener of claim 1 having a first member and a second member and wherein the actuator mechanism comprises
 a journal; and
 a first link and a second link, each link rotatingly and slidingly joined to the journal, the first link rotatingly joined to the first member and the second link rotatingly joined to the second member such that when the journal is moved, the first link and the second link move and cause the first member and the second member to move independently to conform to the cavity.

8. The fastener of claim 1 having a first member and a second member and wherein the actuator mechanism comprises
 a journal; and
 a cam slidingly and rotatingly connected to the journal, the cam further slidingly and rotatingly joined to the first member and to the second member such that when the journal is moved, the cam moves and causes the first member and the second member to move independently to conform to the cavity.

9. The fastener of claim 1 having a first member and a second member and wherein the actuator mechanism comprises
 a journal;
 a first link having a first end and a second end, the first end pivotally connected to the journal;
 a second link having a first end and a second end, the first end pivotally connected to the second end of the first link, and the second end pivotally connected to the first member; and
 a third link having a first end and a second end, the first end connected to the second end of the first link, and the second end pivotally connected to the second member
wherein when the journal is moved, the first link moves and acts on second link and the third link to cause the first member and the second member to move independently to conform to the cavity.

10. The fastener of claim 1 having a first member and a second member and wherein the actuator mechanism comprises
 a journal;
 a first link having a first end and a second end, the first end pivotally and slidingly connected to the journal, and the second end pivotally connected to the first member; and
 a second link having a first end and a second end, the first end pivotally and slidingly connected to the journal, and the second end pivotally connected to the second member;
wherein when the journal is moved, the first link and the second link move to cause the first member and the second member to move independently to conform to the cavity.

11. The fastener of claim 1 having a first member and a second member and wherein the actuator mechanism comprises
 a journal; and
 a cam having a first slot and a second slot, the first slot slidingly and pivotally connected to the journal, and the second slot slidingly and pivotally joined to the first member and to the second member such that when the journal is moved, the cam moves and causes the first member and the second member to move independently to conform to the cavity.

12. The fastener of claim 1 having a first member and a second member, each member having an arm, and wherein the actuator mechanism comprises
 a shaft having a first end and a second end; and
 a component constrained to be in slidable contact with the second end of the shaft and in contact with the arm of each member such that when the shaft is moved, the component moves in contact with the arms and causes the first member and the second member to move independently to conform to the cavity.

13. The fastener of claim 1 having a first member and a second member, each member having an angled surface, and wherein the actuator mechanism comprises
 a shaft having a first end and a second end; and
 a component constrained by the angled surface of each member to be in slidable contact with the second end of the shaft such that when the shaft is moved, the component moves in contact with the members and causes the first member and the second member to move independently to conform to the cavity.

14. A fastener for implanting into a cavity, the fastener comprising:
 a body comprising a movable structure;
 a plurality of members rotatingly connected to the movable structure, each member being independently movable with respect to the body for coordinated self-seeking conforming to the cavity; and
 an actuator mechanism within the movable structure for coordinating and translating applied force to conform independently each member to the cavity, the actuator mechanism comprising
  a journal rotatingly and slidingly connected to each member such that when the journal is moved through the bore of the body, each member moves symmetrically with respect to the structure and moves independently with respect to the body to conform to the cavity.

15. The fastener of claim 7, 8, 9, 10, 11, or wherein the actuator mechanism further comprises a bearing having a bore for housing the journal, the journal further having an end movably connected to the bearing so that when the bearing is moved, the journal moves through the bore of the bearing.

16. A fastener for securing a structure to a cavity, the structure configured to fit to an outer surface of the cavity, the fastener comprising
 a body having a first bore and a slot opening onto the first bore;
 a cylinder within the first bore, the cylinder having a driving mechanism comprising a worm gear;
 a member within the slot, the member comprising a plurality of gear teeth, the member movably connected to the body and acted on by the driving mechanism for conforming to the cavity and wherein the worm gear meshes with the gear teeth of the member and, when a force is applied to the cylinder, the driving mechanism causes the member to move to conform to the cavity, thereby securing the structure to the cavity.

17. The fastener of claim 16 further comprising a locking means for locking the cylinder within the bore.

18. The fastener of claim 16 wherein the structure is a prosthesis.

19. The fastener of claim 1, 14, or 16 formed of a biocompatible material selected from the group consisting of a metal, a ceramic, a polymer, and a combination thereof.

20. Use of the fastener of claim 1, 14, or 16 for implanting into a cavity and aligning the fastener within the cavity comprising placing the fastener into the cavity; and applying force to conform each member of the plurality of members to the cavity thereby aligning the fastener with the cavity.

21. Use of the fastener of claim 1, 14, or 16 for fastening airplane skin at a cavity site, comprising placing the fastener into a cavity of airplane skin; and applying force to conform each member of the plurality of members to the cavity thereby fastening the airplane skin.

22. Use of the fastener of claim 1, 14, or 16 for aligning a part to an object in automated production, comprising placing the fastener onto the part; and applying force to the fastener to conform each member of the plurality of members to align the part to the object.

23. The use of claim 22 where the object is a robot or part thereof.

24. Use of the fastener of claim 1, 14, or 16 wherein the cavity is a hard tissue defect of an animal, for fastening a prosthesis to the hard tissue defect comprising placing the fastener into the hard tissue defect of the animal;

applying force to conform each member of the plurality of members to the cavity; and attaching the prosthesis to the fastener.

25. Use of the fastener of claim 24 wherein a sufficient interfacial pressure exists between each member and the cavity to cause hard tissue density to increase when in use.

\* \* \* \* \*

UNITED STATES PATENT AND TRADEMARK OFFICE
CERTIFICATE OF CORRECTION

PATENT NO. : 5,882,351

DATED : March 16, 1999

INVENTOR(S) :
William Casey Fox

It is certified that error appears in the above-identified patent and that said Letters Patent is hereby corrected as shown below:

On the cover page at item [63]
delete "which is a continuation-in-part of Ser. No. 536,461, Sep. 29, 1995"; and add item --[60] Provisional application No. 60/042,914, Sep. 29, 1995--, in accordance with the present printing style.

In the Abstract, line 2, delete the first occurrence of "or" and substitute --for--, therefor.

In the Abstract, line 8, insert --or-- immediately following 'on,'.

In the Abstract, line 11, insert --a-- immediately following 'apply'.

In the specification, column 1, lines 7-8, delete "is a continution-in-part application of U.S. Ser. No. 08/536,461, filed Sep. 29, 1995, which"

In Claim 9, column 25, line 48, insert the word --pivotally-- immediately preceding 'connected'.

UNITED STATES PATENT AND TRADEMARK OFFICE
CERTIFICATE OF CORRECTION

PATENT NO. : 5,882,351
DATED : March 16, 1999
INVENTOR(S) : William Casey Fox

It is certified that error appears in the above-identified patent and that said Letters Patent is hereby corrected as shown below:

In Claim 15, column 26, line 51, insert the number --14-- immediately following 'or'.

In Claim 16, column 26, line 67, insert --;-- immediately following 'cavity'.

Signed and Sealed this

Twenty-first Day of September, 1999

Attest:

Q. TODD DICKINSON

*Attesting Officer*    *Acting Commissioner of Patents and Trademarks*